(12) United States Patent
Kubota et al.

(10) Patent No.: US 6,958,339 B2
(45) Date of Patent: Oct. 25, 2005

(54) PYRAZOLE DERIVATIVE

(75) Inventors: Hirokazu Kubota, Ibaraki (JP);
Yasuhiro Yonetoku, Ibaraki (JP); Keizo Sugasawa, Ibaraki (JP); Masashi Funatsu, Ibaraki (JP); Souichirou Kawazoe, Ibaraki (JP); Akira Toyoshima, Ibaraki (JP); Jun Ishikawa, Ibaraki (JP); Makoto Takeuchi, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 09/773,736

(22) Filed: Feb. 2, 2001

(65) Prior Publication Data

US 2001/0011090 A1 Aug. 2, 2001

Related U.S. Application Data

(62) Division of application No. 09/529,131, filed as application No. PCT/JP98/04583 on Oct. 12, 1998, now Pat. No. 6,348,480.

(30) Foreign Application Priority Data

Oct. 13, 1997 (JP) .......................................... P. 9-279093

(51) Int. Cl.$^7$ .................... C07D 231/12; C07D 231/14; A61K 31/415
(52) U.S. Cl. .................. 514/255.05; 514/326; 514/341; 514/361; 514/365; 514/374; 514/397; 514/406; 544/405; 548/127; 548/200; 548/236; 548/312.4; 548/364.1; 548/365.7; 548/375.1; 546/211; 546/275.4
(58) Field of Search ................................ 548/127, 200, 548/236, 312.4, 364.1, 365.7, 375.1; 546/211, 275.4; 544/405; 514/255.05, 326, 341, 361, 365, 374, 397, 406

(56) References Cited

U.S. PATENT DOCUMENTS

| | | | | |
|---|---|---|---|---|
| 4,728,653 A | * | 3/1988 | Campbell et al. | ............ 514/312 |
| 5,403,838 A | | 4/1995 | Reinhard et al. | ........ 514/224.2 |
| 5,571,821 A | | 11/1996 | Vitukudi et al. | ............ 514/312 |
| 5,712,279 A | | 1/1998 | Biller et al. | ................. 514/252 |
| 6,140,509 A | * | 10/2000 | Behan et al. | ............ 548/365.7 |
| 6,506,747 B1 | * | 1/2003 | Betageri et al. | ......... 514/228.8 |
| 2001/0044445 A1 | | 11/2001 | Bamaung et al. | ........... 514/277 |

FOREIGN PATENT DOCUMENTS

| | | | | |
|---|---|---|---|---|
| CA | 2249542 | 4/1999 | ......... | C07D/405/04 |
| DE | 34 01 911 | 1/1985 | | |
| JP | 64-55557 | * 3/1989 | | |
| JP | 1-287071 | 11/1989 | | |
| JP | 03-77869 | 4/1991 | | |
| JP | 3-141261 | 6/1991 | | |
| JP | 4-234851 | 8/1992 | | |
| JP | 10-72434 | * 3/1998 | | |
| WO | WO 85/04878 | * 11/1985 | | |
| WO | WO 96/10559 | 4/1996 | | |
| WO | WO 96/23783 | 8/1996 | | |
| WO | WO 96/31517 | 10/1996 | | |
| WO | WO 97/05131 | 2/1997 | | |
| WO | WO 98/37068 | 8/1998 | | |
| WO | 99/51580 | 10/1999 | ......... | C07D/231/16 |
| WO | 99/62885 | 12/1999 | ......... | C07D/231/14 |

OTHER PUBLICATIONS

Cacchi et al., CAPLUS Abstract 127:293164 (Synlett (1997), (8), 959–961), 1997.*
Sykulski et al., CAPLUS Abstract 91:74524, 1979.*
Putney, Jr. et al., Mechanisms of capacitative calcium entry, Journal of Cell Science, 114(12), pp. 2223–2229, 2001.*
McDyer et al., IL–2 Recepto Blockade Inhibits Late, But not early, IFN–g and CD40 Ligand Expression, The Journal of Immunology, 169: 2736–46, 2002.*
Elgert, Autoimmunity, Immunology: Understanding the Immune System, pp. 315–330, 1996.*
Wachlin et al., IL–1b, IFN–1g and TNF–a increase vulnerability of pancreatic beta cells to autoimmune destruction, Journal of Autoimmunity, 20, pp. 303–312, 2003.*
Bremner et al., Therapy of Crohn's Disease in childhood, Expret Opin. Pharmacother. 3(7):809–825, 2002.*
Singh et al., Immune Therapy in inflammatory bowel disease and models of colitis, British Journal of Surgery, 88, 1558–1569, 2001.*
Robinson, Medical Therapy of Inflammatory Bowel Disease for the 21$^{st}$ Century, Eur. J. Surg. Suppl. 582:90–98, 1998.*
Beers et al., Crohn's Disease, Ulcerative colitis, The Merck Manual of Diagnosis and Therapy, Seventeenth Edition (online), 1999.*

(Continued)

*Primary Examiner*—Deepak Rao
(74) *Attorney, Agent, or Firm*—Sughrue Mion, PLLC

(57) ABSTRACT

The present invention is directed to drugs, in particular, pyrazole derivatives represented by the following general formula (I)

$$\underset{N}{\overset{N}{\diagdown}}\!\!\diagup\!\!\overset{}{\underset{}{D}}\!\!-\!\!(CH_2)_n\!-\!\!\overset{}{\underset{}{B}}\!\!-\!\!X\!\!-\!\!A \qquad (I)$$

which have a calcium release-activated calcium channel inhibitory effect and medicinal compositions, in particular, calcium release-activated calcium channel inhibitors containing the above compounds as the active ingredient, wherein each substituent is defined in the specification.

The present invention also relates to a pharmaceutical composition containing an effective amount of the compound of formula (I) and a pharmaceutically effective carrier.

The present invention further relates to methods of treatment of diseases associated with calcium release-activated calcium channels, diseases associated with IL-2 production, and methods of treatment of allergic, inflammatory or autoimmune diseases.

15 Claims, No Drawings

OTHER PUBLICATIONS

Patel et al., Synthesis of substituted 6–(3', 5'–dimethyl–1H–pyrazol–1'–yl)quinolines and evaluation of their biological activities, Indian Journal of Chemistry, vol. 29B, pp. 836–842, Sep. 1990.*
Finar et al., Chem. Abstract 55:25921f, 1961.*
Bouchet et al., Chem. Abstract 85:5545w, 1976.*
Patel et al., Chem. Abstract 114:23862u, 1991.*
Kawamura et al., Chem. Abstract 128:230375, 1998.*
Mizukawa et al., Chem. Abstract 111:205323, 1989.*
Bartroli et al, *J. Med. Chem.*, 41(11):1855–1868 (1998).
Wright et al, *J. Med. Chem.*, 7(1):102–105 (1964).
Okazaki, "Nonlinear Optical Material and Triazole Compound", Chemical Abstract No. 325369, vol. 123, No. 24 (Dec. 11, 1995).
Nicolai et al, *Chem. Pharm. Bull.*, 42(8):1617–1630 (1994).
Badachikar et al, *Indian J. Chem.*., 25B:1079–1080 (1996).
Mokhtar et al, *Pharmazie*, 33(10):649–651 (1978).

* cited by examiner

US 6,958,339 B2

PYRAZOLE DERIVATIVE

This is a divisional application of application Ser. No. 09/529,131, filed Apr. 7, 2000, now U.S. Pat. No. 6,348,480, which is a 371 of PCT/JP98/04583, filed Oct. 12, 1998, the disclosure of which is incorporated herein by reference.

TECHNICAL FIELD

This invention relates to a medicament, particularly a pyrazole derivative having an action to inhibit calcium release-activated calcium channel, and a pharmaceutical composition containing the same as an active ingredient, particularly a calcium release-activated calcium channel inhibitor.

BACKGROUND ART

It has been known for a long time that calcium ion ($Ca^{2+}$) is important for an intracellular second messenger in the activation of various cells. Intracellular $Ca^{2+}$ also acts as an important regulatory factor in inflammatory cells. It has been suggested, however, that voltage-operated $Ca^{2+}$ channel (to be referred to as "VOCC" hereinafter) inhibitors such as nifedipine does not show inhibitory activity against the activation of inflammatory cells and that a $Ca^{2+}$ influx mechanism other than VOCC exist in inflammatory cells.

Hoth et al. have reported that a $Ca^{2+}$-selective and $Ca^{2+}$ store depletion-activated $Ca^{2+}$ channel, namely $Ca^{2+}$ release-activated $Ca^{2+}$ channel (to be referred to as "CRACC" hereinafter; also called store-dependent $Ca^{2+}$ channel), is present in mast cells and lymphocytes, and these cells are insensitive to membrane potential (*Pflugers Arch.*, 430, pp. 315–322 (1995)). It is known that CRACC is present in several inflammatory cells such as mast cells, lymphocytes, astrocytes (*J. Biol. Chem.*, 270, pp. 29–32 (1995)) and the like, and that it is deeply concerned in, for example, cytokine production and lipid mediator release (*J. Immunol.*, 155, pp. 285–296 (1995) and *Br. J. Pharmacol.*, 114, pp. 598–601 (1995)).

Recently, it has been revealed that tenidap, an agent for treating rheumatoid arthritis, has a potency of CRACC inhibitor (*Cell Calcium*, 14, pp. 1–16 (1993)). Therefore, a CRACC inhibitor has a possibility of therapeutic potency on chronic inflammatory diseases including rheumatoid arthritis.

It is known that CRACC is also present in endothelial cells (*Am. J. Physiol.*, 269, C 733–738 (1995)) and epithelial cells (*J. Biol. Chem.*, 270, pp. 29169–175 (1995)). Since it has been reported that sustained calcium influx takes a role in the radical affection of endothelial cells (*Am. J. Physiol.*, 261, C 889–896 (1991)), it is suggested that a CRACC inhibitor should have protective efficacy on endothelial cell-concerned tissue damage.

In addition, it has been reported that blockades of calcium influx inhibit cell proliferation and interleukin 2 (IL-2) production (*Br. J. Pharmacol.*, 113, pp. 861–868 (1994)). Therefore, a CRACC inhibitor is useful as an agent for the prevention and treatment of proliferative or progressive diseases (e.g., malignant tumor and the like) and autoimmune diseases, and also as a suppresser for tissue rejection in transplantation.

On the other hand, it is known that in excitable cells such as smooth muscle cells and nerve cells, intracellular calcium is mainly regulated with VOCC not with CRACC. Therefore, it is expected that a calcium channel blocker having CRACC selectivity against VOCC should be an useful agent for the prevention or treatment of various inflammatory diseases, allergic diseases, autoimmune diseases, tissue damages, proliferative diseases and the like without undesirable actions on cardiovascular and central nervous system.

Recently, some compounds showing CRACC inhibitory activity have been reported, such as a cycloalkyl-piperazinylethanol derivative disclosed in a published German patent application 4404249 and a 2-(3,4-dihydro-1-isoquinolyl)acetamide derivative disclosed in WO 94/00435. It has also reported that 5-amino-1-[[3,5-dichloro-4-(4-chlorobenzoyl)phenyl]methyl]-1H-1,2,3-triazole-4-carboxamide inhibits CRACC (*J. Pharm. Exp. Ther.*, 257, pp. 967–971 (1991)). However, there are no reports on a compound whose CRACC selectivity over VOCC has been confirmed.

On the other hand, a published German patent application 2525024 discloses a 5-(heterocycloylaminophenyl)-1-phenylpyrazole derivative which shows an anti-inflammatory activity. However, this patent does not disclose or suggest about its inhibitory activities against CRACC and IL-2 production.

WO 95/18097 discloses an anthranilic acid derivative represented by the following formula, which inhibits a cyclic GMP phosphodiesterase. In the formula, $R_1$ to $R_4$ represent H, a halogen atom, . . . , pyrazolyl which may be substituted, . . . ; n is 0 to 6, W represents N or CH, Y represents O or S, . . . (see said published patent application for details).

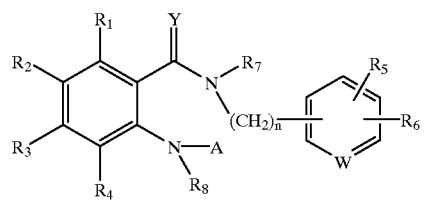

An unexamined published Japanese patent application 9-59236 discloses an $R^1$, $R^2$-di-substituted benzamide derivative represented by the following formula, which is useful for the prevention and treatment of rheumatic, allergic and other inflammatory diseases. In the formula, $R^1$ represents a substituted or unsubstituted aromatic heterocyclic ring, . . . , $R^2$ represents a halogen, a nitro, —$NR^5R^6$, . . . , A represents —$C(=Z)NR^3R^4$ or —$NR^4C(=Z)R^3$, $R^3$ represents a substituted or unsubstituted aromatic hydrocarbon ring, a substituted or unsubstituted aromatic heterocyclic ring . . . (see said published patent application for details). However, there is no illustrative disclosure about pyrazolyl as the aromatic heterocyclic ring group. In addition, there is no disclosure about inhibitory activities against CRACC and/or IL-2 production.

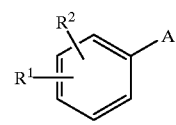

DISCLOSURE OF THE INVENTION

The inventors of the present invention have conducted extensive studies on the screening of compounds having excellent CRACC inhibitory activity. As a result of the efforts, certain pyrazole derivatives which possess entirely different structures from those of the reported CRACC inhibitors have been found to show excellent CRACC inhibitory activity. The present invention has been accomplished by further finding that these compounds have high CRACC selectivity over VOCC.

Accordingly, the invention relates to a novel pyrazole derivative represented by the following general formula (I) which is characterized in that it has a pyrazolyl group unsubstituted or substituted with a specified group, or a pharmaceutically acceptable salt thereof. In the specification of this application, lower alkyl and halogen atom are abbreviated as Alk and Hal, respectively.

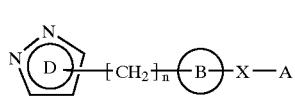
(I)

(In the formula, each symbol has the following meaning:
D: pyrazolyl which may have 1 to 3 substituents selected from the group consisting of -Alk, -lower alkenyl, -lower alkynyl, -halogeno-lower alkyl, -Alk-cycloalkyl, -Alk-O-Alk, -cycloalkyl, —O-Alk, —COOH, —COO-Alk and -Hal,
n: 0 or 1,
B: phenylene, a nitrogen-containing, divalent, saturated ring group, or a monocyclic, divalent heteroaromatic ring group which may be substituted with Alk,
X: —NR$^1$—CR$^2$R$^3$—, —CR$^2$R$^3$—NR$^1$—, —NR$^1$—SO$_2$—, —SO$_2$—NR$^1$— or —CR$^4$=CR$^5$—,
R$^1$: —H, —OH, -Alk, —O-Alk or —CO-Alk,
R$^2$ and R$^3$: the same or different from each other and each represents —H or -Alk, or R$^2$ and R$^3$ together form =O or =S,
R$^4$ and R$^5$: the same or different from each other and each represents —H, -Hal, -halogeno-lower alkyl or -Alk, and
A: benzene ring which may have one or more substituents; mono-, di- or tricyclic fused heteroaryl which may have one or more substituents; cycloalkyl which may have one or more substituents; a nitrogen-containing, saturated ring group which may have one or more substituents; lower alkenyl which may have one or more substituents; lower alkynyl which may have one or more substituents; or Alk which may have one or more substituents,
or A and X may together form a group represented by a formula

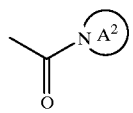

(wherein A$^2$ is a nitrogen-containing hetero ring selected from the group consisting of 1-pyrrolidinyl, pyrazolidinyl, piperidino, piperazinyl, morpholino, 3,4-dihydro-2H-1,4-benzoxazin-4-yl and indolinyl, wherein the hetero ring may have one or more substituents), with the proviso that
(1) when D is 3,5-bis(trifluoromethyl)-1H-pyrazol-1-yl, n is 0, B is 1,4-phenylene and X is NHCO, A is a group other than 4-methyl-1,2,3-thiadiazol-5-yl,
(2) when D is 1-methyl-5-trifluoromethyl-1H-pyrazol-3-yl, n is 0, B is thiophene-2,5-diyl and X is CONH, A is a group other than 4-chlorophenyl,
(3) when D is 1-methyl-3-trifluoromethyl-1H-pyrazol-5-yl, n is 0, B is thiophene-2,5-diyl and X is CONH, A is a group other than benzyl,
(4) when D is 4-ethoxycarbonyl-5-trifluoromethyl-1H-pyrazol-1-yl, n is 0, B is 1,4-phenylene and Y is NHCO, A is a group other than trichlorovinyl,
(5) when D is 1H-pyrazol-1-yl, n is 0, B is 1,4-phenylene and Y is NHCO, A is a group other than 2-ethoxyvinyl, and
(6) when n is 1, D is 1H-pyrazol-5-yl substituted with at least one trifluoromethyl group or 1H-pyrazol-1-yl substituted with at least one trifluoromethyl group. The same shall apply hereinafter.)

The invention also relates to a pharmaceutical composition, particularly a pharmaceutical composition for use in the inhibition of calcium release activated calcium channel, which comprises a pyrazole derivative represented by the following general formula (I') or a pharmaceutically acceptable salt thereof and a pharmaceutically acceptable carrier. Preferably, it relates to an IL-2 production inhibitor, a preventive or therapeutic agent for allergic, inflammatory or autoimmune diseases and a preventive or therapeutic agent for bronchial asthma or rheumatoid arthritis.

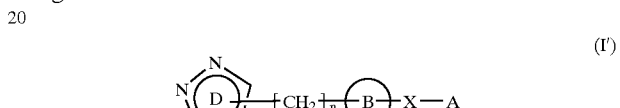
(I')

(In the formula, each symbol has the following meaning:
D: pyrazolyl which may have 1 to 3 substituents selected from the group consisting of -Alk, -lower alkenyl, -lower alkynyl, -halogeno-lower alkyl, -Alk-cycloalkyl, -Alk-O-Alk, -cycloalkyl, —O-Alk, —COOH, —COO-Alk and -Hal,
n: 0 or 1,
B: phenylene, a nitrogen-containing, divalent, saturated ring group, or a monocyclic, divalent heteroaromatic ring group which may be substituted with Alk,
X: —NR$^1$—CR$^2$R$^3$—, —CR$^2$R$^3$—NR$^1$—, —NR$^1$—SO$_2$—, —SO$_2$—NR$^1$— or —CR$^4$=CR$^5$—,
R$^1$: —H, —OH, -Alk, —O-Alk or —CO-Alk,
R$^2$ and R$^3$: the same or different from each other and each represents —H or -Alk, or R$^2$ and R$^3$ together form =O or =S,
R$^4$ and R$^5$: the same or different from each other and each represents —H, -Hal, -halogeno-lower alkyl or -Alk, and
A: benzene ring which may have one or more substituents; mono-, di- or tricyclic fused heteroaryl which may have one or more substituents; cycloalkyl which may have one or more substituents; a nitrogen-containing, saturated ring group which may have one or more substituents; lower alkenyl which may have one or more substituents; lower alkynyl which may have one or more substituents; or Alk which may have one or more substituents, or A and X may together form a group represented by a formula

(wherein A$^2$ is a nitrogen-containing hetero ring selected from the group consisting of 1-pyrrolidinyl, pyrazolidinyl, piperidino, piperazinyl, morpholino, 3,4-dihydro-2H-1,4-benzoxazin-4-yl and indolinyl, wherein the hetero ring may have one or more substituents), with the proviso that when n is 1, D is 1H-pyrazol-5-yl substituted with at least one trifluoromethyl group or 1H-pyrazol-1-yl substituted with at least one trifluoromethyl group. The same shall apply hereinafter.)

The following known compounds are included in the aforementioned general formula (I').
(1) A compound wherein D: 3,5-bis(trifluoromethyl)-1H-pyrazol-1-yl, n: 0, B: 1,4-phenylene, Y: NHCO and A: 4-methyl-1,2,3-thiadiazol-5-yl (to be referred to as compound A hereinafter),
(2) a compound wherein D: 1-methyl-5-trifluoromethyl-1H-pyrazol-3-yl, n: 0, B: thiophene-2,5-diyl, Y: CONH and A: 4-chlorophenyl (to be referred to as compound B hereinafter),
(3) a compound wherein D: 1-methyl-3-trifluoromethyl-1H-pyrazol-5-yl, n: 0, B: thiophene-2,5-diyl, Y: CONH and A: benzyl (to be referred to as compound C hereinafter),
(4) a compound wherein D: 4-ethoxycarbonyl-5-trifluoromethyl-1H-pyrazol-1-yl, n: 0, B: 1,4-phenylene, Y: NHCO and A: trichlorovinyl (to be referred to as compound D hereinafter), and
(5) a compound wherein D: 1H-pyrazol-1-yl, n: 0, B: 1,4-phenylene, Y: NHCO and A: 2-ethoxyvinyl (to be referred to as compound E hereinafter).

However, though the compounds A to D are described in the MAYBRIDGE's reagent catalog (UK, Cornwall, published in August, 1995) as SEW04225, KM02940, KM03000 and GK02421, there are no reports on their application to not only medicaments as a matter of course but also other use. Also, the compound E is disclosed as a production material of a medicament in JP-A-61-82, but there is no description regarding its pharmacological actions. Thus, the pharmaceutical compositions which contain these known compounds are novel.

Preferred compounds of the general formula (I) or (I') of the invention are pyrazole derivatives or pharmaceutically acceptable salts thereof, in which the pyrazolyl group of D is pyrazolyl (particularly 1H-pyrazol-5-yl or 1H-pyrazol-1-yl) which is substituted with at least one trifluoromethyl group.

Other preferred compounds of the invention are listed below.

Pyrazole derivatives or pharmaceutically acceptable salts thereof, in which
1) A is phenyl which may have one or more substituents of F group; mono-, di- or tricyclic fused heteroaryl which may have one or more substituents of F group; cycloalkyl which may have one or more substituents of F group; a nitrogen-containing, saturated ring group which may have one or more substituents of F group; lower alkenyl which may have one or more substituents of G group; lower alkynyl which may have one or more substituents of G group; or Alk which may have one or more substituents of G group, wherein
the F group is a group consisting of -Alk, -lower alkenyl, -lower alkynyl, -Hal, —NH$_2$, —NH(Alk), —N(Alk)$_2$, —NO$_2$, —CN, —OH, —O-Alk, —O—CO-Alk, —SH, —S-Alk, —COOH, —COO-Alk, —CO-Alk, —CHO, —CONH$_2$, —CONH(Alk), —CON(Alk)$_2$, —SO-Alk, —SO$_2$-Alk, —SO$_2$NH$_2$, —SO$_2$NH-(Alk), —SO$_2$N(Alk)$_2$, -aryl, -cycloalkyl, —O-Alk-O—, -halogeno-lower alkyl, -Alk-NH$_2$, -Alk-NH(Alk), -Alk-N(Alk)$_2$, -Alk-OH, -Alk-O-Alk, -Alk-SH, -Alk-S-Alk, -Alk-COOH, -Alk-COO-Alk, -Alk-CO-Alk, -Alk-CHO, -Alk-CONH$_2$, -Alk-CONH(Alk), -Alk-CON(Alk)$_2$, -Alk-SO-Alk, -Alk-SO$_2$-Alk, -Alk-SO$_2$NH2, -Alk-SO$_2$NH(Alk), -Alk-SO$_2$N(Alk)$_2$, -Alk-aryl and -Alk-cycloalkyl, and the G group is a group consisting of -Hal, —NH$_2$, —NH(Alk), —N(Alk)$_2$, —NO$_2$, —CN, —OH, —O-Alk, —O—CO-Alk, —SH, —S-Alk, —COOH, —COO-Alk, —CO-Alk, —CHO, —CONH$_2$, —CONH(Alk), —CON(Alk)$_2$, —SO-Alk, —SO$_2$-Alk, —SO$_2$NH$_2$, —SO$_2$NH-(Alk), —SO$_2$N(Alk)$_2$, aryl which may have one or more substituents of F group; mono-, di- or tricyclic fused heteroaryl which may have one or more substituents of F group; cycloalkyl which may have one or more substituents of F group and a nitrogen-containing, saturated ring group which may have one or more substituents of F group,
or A and X may together form a group represented by a formula

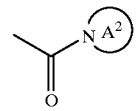

(wherein A$^2$ is a nitrogen-containing hetero ring selected from the group consisting of 1-pyrrolidinyl, pyrazolidinyl, piperidino, piperazinyl, morpholino, 3,4-dihydro-2H-1,4-benzoxazin-4-yl and indolinyl, wherein the hetero ring may have one or more substituents of F group),
2) B is phenylene; piperidine-1,4-diyl; or a monocyclic, divalent heteroaromatic ring selected from the group consisting of thiophene, furan, pyrrole, imidazole, pyrazole, thiazole, isothiazole, oxazole, isoxazole, thiadiazole, pyridine, pyrazine, pyridazine and pyrimidine, which may be substituted with Alk, X is —NH—CO—, —NH—CH$_2$—, —N(OH)—CO—, —N(Alk)—CO—, —CO—NH—, —CH$_2$—NH—, —CO—N(OH)—, —CO—N(Alk)—, —SO$_2$NH—, —NHSO$_2$— or —CH=C(Hal)—, A is aryl which may have one or more substituents of group F; mono-, di- or tricyclic fused heteroaryl selected from the group consisting of thienyl, furanyl, pyrrolyl, imidazolyl, pyrazolyl, thiazolyl, isothiazolyl, oxazolyl, isoxazolyl, tetrazolyl, triazolyl, thiadiazolyl, pyridyl, pyrazinyl, pyrimidinyl, pyridazinyl, indolyl, isoindolyl, isoquinolyl, quinolyl, quinoxanyl, phthalazinyl, imidazopyridyl, quinazolinyl and cinnolinyl, which may have one or more substituents of group F; cycloalkyl; a nitrogen-containing, saturated ring selected from the group consisting of pyrrolidinyl, imidazolidinyl, pyrazolidinyl, piperidyl, piperazinyl and morpholinyl, which may be substituted with one or more Alk; lower alkynyl which may be substituted with one or more Hal; lower alkenyl which may be substituted with one or more Hal; or Alk which may be substituted with one or more Hal, and the F group is a group consisting of -Alk, -lower alkenyl, -lower alkynyl, -Hal, —NH$_2$, —NH(Alk), —N(Alk)$_2$, —NO$_2$, —CN, —OH, —O-Alk, —O—CO-Alk, —SH, —S-Alk, —COOH, —COO-Alk, —CO-Alk, —CHO, —CONH$_2$, —CONH(Alk), —CON(Alk)$_2$, —SO-Alk, —SO$_2$-Alk, —SO$_2$NH$_2$, —SO$_2$NH-(Alk) and —SO$_2$N(Alk)$_2$, or A and X may together form a group represented by a formula

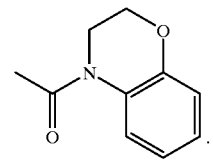

3) n is 0, D is pyrazolyl which may have 1 to 3 substituents selected from -Alk, -halogeno-lower alkyl, —COOH and —COO-Alk, B is phenylene or a monocyclic, divalent heteroaromatic ring selected from the group consisting of thiophene, furan, thiazole, pyridine and pyrimidine, which may be substituted with Alk, X is —NH—CO—, —N(OH)—CO—, —CO—NH—, —CH$_2$—NH— or —CO—N(Alk)—, and A is phenyl which may have one or more substituents selected from the group consisting of -Alk, -Hal, —NH$_2$, —N(Alk)$_2$, —NO$_2$, —CN, —OH, —O-Alk and —COO-Alk; mono-, di- or tricyclic fused heteroaryl selected from the group consisting of thienyl, pyrrolyl, imidazolyl, thiazolyl, oxazolyl, tetrazolyl, triazolyl, thiadiazolyl, pyridyl, pyrazinyl and isoquinolyl, which may be substituted with Alk; cycloalkyl; lower alkenyl which may be substituted with one or more Hal; or Alk, or 4) X is —NH—CO— or —CO—NH—.

Particularly preferred is a pyrazole derivative or a pharmaceutically acceptable salt thereof, in which D is 1-methyl-3-trifluoromethyl-1H-pyrazol-5-yl and A is phenyl which may be substituted with Hal, or D is 3,5-bis(trifluoromethyl)-1H-pyrazol-1-yl and A is monocyclic heteroaryl selected from the group consisting of thiazolyl, thiadiazolyl, thienyl and pyridyl, which may be substituted with Alk.

Unless otherwise noted, the term "lower" as used herein means a straight or branched carbon chain having from 1 to 6 carbon atoms. Examples of preferred groups include methyl, ethyl, propyl and the like as "lower alkyl (Alk)", vinyl, 1-propenyl, 1,2-dimethyl-1-propenyl and the like as "lower alkenyl" and ethynyl and the like as "lower alkynyl". The "halogen atom (Hal)" is I, Br, F or Cl. The "halogeno-lower alkyl" is an Alk substituted with one or more Hal, and trifluoromethyl is particularly preferable. The "aryl" is an aryl group having from 6 to 14 carbon atoms, preferably phenyl or naphthyl. The "cycloalkyl" is a cycloalkyl having from 3 to 8 carbon atoms, preferably cyclopropyl or cyclohexyl.

The "monocyclic, divalent heteroaromatic ring group" is a five- or six-membered monocyclic, divalent heteroaromatic ring group which contains from 1 to 4 hetero-atoms selected from N, S and O atoms, and furan-2,5-diyl, thiophene-2,5-diyl, thiazole-2,5-diyl, pyridine-2,5-diyl and pyrimidine-2,5-diyl are particularly preferable. The "phenylene" is preferably 1,4-phenylene.

The "mono-, di- or tricyclic fused heteroaryl" is a five- or six-membered mono-, di- or tricyclic fused ring which contains from 1 to 5 of O, S or N atom as heterocyclic atoms. The "nitrogen-containing saturated ring" is a five- or six-membered nitrogen-containing saturated ring which contains 1 or 2 N atoms as ring atoms and may further contain one O or S atom. The "nitrogen-containing, divalent, saturated ring group" is preferably piperidine-1,4-diyl. When n is 0, D and B are directly bonded.

The compound of this invention may exist in the form of geometrical isomers or tautomers depending on the kinds of substituent groups, and these isomers in separated forms or mixtures thereof are included in the present invention. Also, the compound of the present invention may have asymmetric carbon atoms, so that it may exist in (R) and (S) optical isomer forms based on such carbon atoms. All of the mixtures and the isolated forms of these optical isomers are included in the present invention.

The compound (I) or (I') of this invention may form an acid addition salt or, depending on the kinds of substituent groups, a salt with a base. Such salts are pharmaceutically acceptable ones, and their preferred examples include acid addition salts with inorganic acids (e.g., hydrochloric acid, hydrobromic acid, hydroiodic acid, sulfuric acid, phosphoric acid and the like) or with organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid and the like) and salts with inorganic bases (e.g., sodium, potassium, magnesium, calcium, aluminum and the like) or with organic bases (e.g., methylamine, ethylamine, ethanolamine, lysine, ornithine and the like), as well as ammonium salts.

In addition, various hydrates and solvates and polymorphism of the compound (I) or (I') and salts thereof are also included in this invention.

(Production Method)

The compound of the present invention and a pharmaceutically acceptable salt thereof can be produced by making use of the features of its basic structure or the kinds of its substituents and by employing various known synthesis methods. In that case, depending on the kind of each functional group, it may sometimes be effective from the viewpoint of production techniques to replace said functional group with an appropriate protecting group, namely a group which can be converted into said functional group easily, at the stage of raw materials or intermediates. Thereafter, the compound of interest can be obtained by removing the protecting group as occasion demands. Examples of such functional groups include a hydroxyl group, a carboxyl group and the like and examples of their protecting groups include those which are described in "Protective Groups in Organic Synthesis", 2nd edition, edited by Greene and Wuts, which may be optionally used depending on the reaction conditions.

The following describes typical methods for the preparation of the compound of the present invention.

Production Method 1

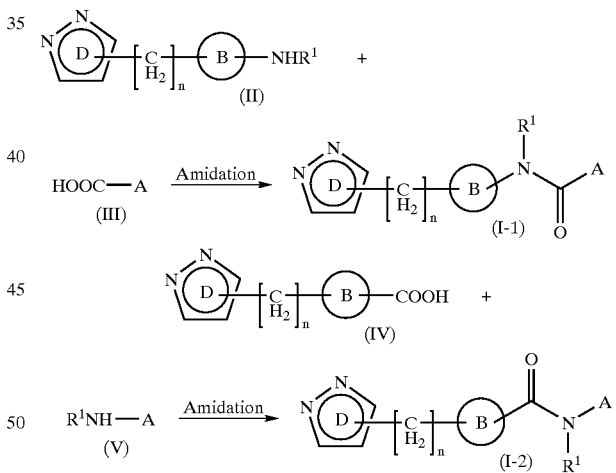

In this method, as shown in the above reaction formula, the compound (I-1) or (I-2) of the present invention is obtained by subjecting an amine derivative represented by the general formula (II) or (V) and a carboxylic acid derivative represented by the general formula (III) or (IV) to amidation reaction.

The carboxylic acid derivative (III) or (IV) which can be used in the production method 1 is a free carboxylic acid or a reactive derivative thereof, and examples of the reactive derivative include acid halides such as acid chlorides, acid bromides and the like; acid azides; active esters which can be prepared using methanol, ethanol, benzyl alcohol, phenol which may be substituted, 1-hydroxybenzotriazole, N-hydroxysuccinimide and the like; symmetric acid anhydrides; and mixed acid anhydrides with alkylcarboxylic acid, p-toluenesulfonic acid and the like. These reactive derivatives are commercially available or can be produced by the usual procedures.

The amidating reaction can be carried out by the usual procedures.

When the reaction is carried out using a free carboxylic acid, it is necessary to use a condensing agent such as N,N'-dicyclohexylcarbodiimide (DCC), 1-(3-dimethylaminopropyl)-3-ethylcarbodiimide (WSCD) or the like or carboxylic acid activating agent such as 1,1'-carbonyldiimidazole, N,N'-disuccinimidyl carbonate, diphenylphosphoryl azide, phosphorus oxychloride, phosphorus trichloride, triphenylphosphine/N-bromosuccinimide or the like.

The reaction is carried out using an amine derivative represented by the general formula (II) or (V) and a carboxylic acid derivative represented by the general formula (III) or (IV), in equimolar amounts or one of them in excess amount, in a reaction inert organic solvent such as pyridine, tetrahydrofuran (THF), dioxane, ether, benzene, toluene, dichloromethane, 1,2-dichloroethane (DCE), chloroform, N,N-dimethylformamide (DMF), ethyl acetate, acetonitrile or the like. The reaction temperature is optionally selected depending on the kinds of reaction derivatives.

Depending on the kinds of reaction derivatives, addition of a base such as triethylamine, pyridine, picoline, N,N-dimethylaniline, potassium carbonate, sodium hydroxide or the like may be advantageous in some cases from the viewpoint of accelerating the reaction. It is possible to use pyridine also as the solvent.

Production Method 2

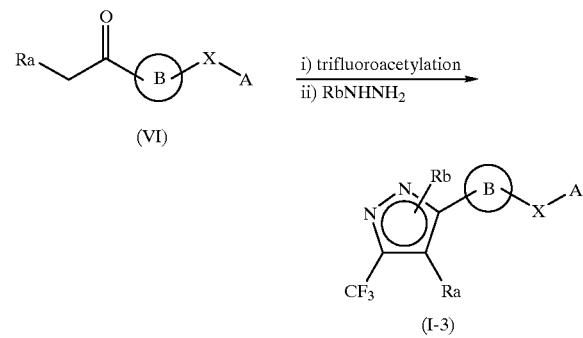

(In the above reaction formula, each of Ra and Rb represents H or Alk.)

In this production method, the compound (I-3) of the present invention is obtained by carrying out trifluoroacetylation of the carbon atom adjacent to the ketone of a compound represented by the general formula (VI) and then effecting cyclization by reacting it with a hydrazine derivative.

The first step trifluoroacetylation can be carried out by allowing the compound to react with a trifluoroacetylation agent (for example, ethyl trifluoroacetate, trifluoroacetic anhydride or the like) at a temperature of from −78° C. to reflux temperature in a solvent such as methanol, ethanol, 1,3-dimethylimidazolidin-2-one (DMI), THF, DMF or the like, in the presence of a base such as sodium methoxide, sodium ethoxide, alkali metal hexamethyldisilazide, alkali metal hydride, alkyl lithium, triethylamine or the like.

The second step cyclization reaction can be carried out by allowing the compound obtained in the first step to react with a hydrazine derivative in a solvent such as methanol, ethanol or the like, or without solvent, in the presence or absence of an acid such as acetic acid, hydrochloric acid or the like or Lewis acid such as titanium(IV) isopropoxide, titanium(IV) chloride, boron trifluoride-diethyl ether complex or the like. This reaction can be carried out at a temperature of from cooling temperature to reflux temperature.

Production Method 3

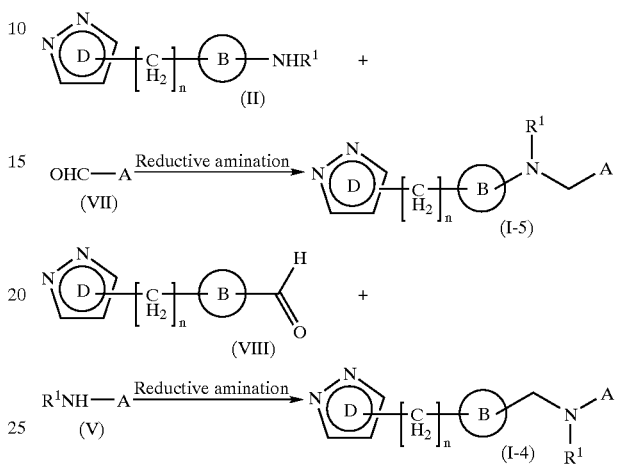

As shown in the above reaction formula, this production method is a method in which the compound (I-4) or (I-5) of the invention is obtained by a reductive amination reaction of an amine derivative represented by the general formula (II) or (V) with an aldehyde derivative represented by the general formula (VII) or (VIII).

This reductive amination reaction is carried out by allowing both compounds to react with each other in the same inert solvent of the case of amidation of the production method 1, and reducing the thus formed Schiff base after its isolation or directly without isolation. It is advantageous to carry out formation of Schiff base in the presence of the aforementioned Lewis acid, p-toluenesulfonic acid, adipic acid, acetic acid, hydrochloric acid or the like acid catalyst, in the presence of molecular sieves, potassium hydroxide or the like dehydrating agent or by removing formed water using Dean-Stark trap. The reaction temperature can be optionally set but is preferably from room temperature to reflux temperature.

Reduction of the Schiff base can be carried out at a temperature of from −20° C. to heat reflux, by adding a reducing agent such as a metal hydride complex (e.g., sodium cyanoborohydride, sodium triacetoxyborohydride or sodium borohydride) or borane. Alternatively, it can be effected by carrying out the reaction using a reduction catalyst (e.g., palladium-carbon or Raney nickel) at a temperature of from 0° C. to 100° C. in a hydrogen atmosphere of from ordinary pressure to 50 kg/cm$^2$, in a solvent such as methanol, ethanol, ethyl acetate, acetic acid or the like in the presence or absence of an acid such as acetic acid, hydrochloric acid or the like.

A compound of the invention in which X is —SO$_2$—NR$^1$— or —NR$^1$—SO$_2$— can be produced in the same manner as the aforementioned production method 1, except that a sulfonic acid derivative is used instead of the carboxylic acid derivative.

A compound in which X is —CR$^4$=CR$^5$— can be produced by effecting formation of an olefin from an organic phosphorus compound and an aldehyde by the Horner-Emmons reaction or Wittig reaction. This reaction can be carried out at a temperature of from −78° C. to heat reflux in THF, DMF or the like solvent in the presence of a base such as lithium diisopropylamide, sodium hydride, triethylamine, alkyl lithium or phenyl lithium.

N-Alkylation of the nitrogen atom of amino group or amido group of X and N-alkylation of the ring nitrogen atoms can be carried out by a usually used N-alkylation method, for example, by allowing an amine derivative to react with an alkyl compound having a usual leaving group such as a halogen atom or an organic sulfone residue, at a temperature of from cooling to reflux in DMF, acetone, 2-butanone, acetonitrile or the like inert solvent or without solvent in the presence or absence of potassium carbonate, triethylamine, sodium hydride or the like base.

In addition to be above, introduction of substituents into respective rings, modification of groups, elimination of protecting groups and the like techniques can be carried out in the usual way.

(Production Method of Starting Compounds)

Starting compounds of the aforementioned production methods are commercially available or can be produced easily by methods well known to those skilled in the art.

Each of the reaction products obtained by the aforementioned production methods is isolated and purified as a free compound, a salt thereof, a hydrate thereof or a solvate thereof. The salt can be produced by a usual salt forming method. The isolation and purification are carried out by employing usually used chemical techniques such as extraction, concentration, evaporation, crystallization, filtration, recrystallization, various types of chromatography and the like. Various forms of isomers can be isolated by the usual procedures making use of physicochemical differences among isomers. For example, optical isomers can be separated by means of a conventional racemic resolution method such as fractional crystallization or a chromatography. In addition, an optical isomer can also be synthesized from an appropriate optically active starting compound.

INDUSTRIAL APPLICABILITY

The compound of the present invention is useful as an active ingredient of pharmaceutical compositions. Since it has inhibitory activities on CRACC and IL-2 production, it is particularly useful as an inhibitor of CRACC or IL-2 production.

It also is particularly useful as an agent for use in the prevention and treatment of allergic, inflammatory or autoimmune diseases in which CRACC and/or IL-2 production are concerned. In this connection, examples of the allergic, inflammatory or autoimmune diseases include various diseases in which CRACC and/or IL-2 production are concerned such as bronchial asthma, psoriasis, atopic diseases including atopic dermatitis, inflammatory bowel diseases including Crohn disease, peptic ulcer, glomerular nephritis, hepatitis, pancreatitis, collagen disease, rheumatoid arthritis, osteoarthritis, rejection on transplantation and the like.

Applicability of the compound of the present invention to the aforementioned diseases is evident from the results of in vitro tests on inhibition of CRACC and IL-2 production, which will be described later, as well as the results of various tests carried out using animal models for diseases such as an antigen-induced airway eosinophilia as a typical model for bronchial asthma, some T-cell-dependent disease models and a collagen-induced arthritis in mice. In addition, since the compounds of the present invention also have inhibitory effects on IL-4, IL-5, MMP-1 and TNFα production, such results also support its applicability to the aforementioned diseases.

On the other hand, anti-proliferative effect of the CRACC inhibitor suggests that it should be useful in preventing or treating proliferative or progressive diseases such as malignant tumor, arteriosclerosis, multiple organ sclerosis, various types of fibrosis, burn keloid and the like. Also, since the CRACC inhibitor inhibits activation of inflammatory cells such as mast cells, leukocytes and astrocytes, which concern with inflammation in several peripheral or brain tissues, its action to protect tissues from their damages such as ischemia-reperfusion injury, head injury, cerebral infarction and myocardial infarction can be expected.

In particular, the compound of the present invention which is possessed of CRACC selective inhibitory activity over VOCC is useful, because it can cause CRACC inhibition without VOCC inhibition-induced undesirable reactions in central nervous system and cardiovascular system and the like.

The following shows certain tests and their results in order to confirm pharmacological actions of the compound of the present invention.

(1) CRACC inhibitory activity

Jurkat cells ($6 \times 10^6$/ml) suspension loaded with a calcium indicator fluorescence dye fura-2 (1 $\mu$M) was dispensed in 100 $\mu$l portions into wells of a 96 well microplate. Intracellular calcium increase stimulated with a calcium pump inhibitor (thapsigargin) was induced by adding to each well a 100 $\mu$l of Hanks' balanced salt solution containing a drug to be tested in two times higher concentration than the final concentration and 2 $\mu$M of thapsigargin (final concentration, 1 $\mu$M), and, after 30 minutes of the addition, a fluorescence intensity ratio (R) was calculated from two fluorescence intensities obtained at excitation wave lengths of 340 nm/500 nm and 380 nm/500 nm, respectively. In calculating R, self-fluorescence of the drug to be tested was measured in a cell-free system, and the effect of the self-fluorescence on the fura-2 fluorescence was corrected.

The intracellular calcium concentration was obtained by the following calculation formula based on a maximum reaction of R (Rmax) obtained by 25 $\mu$M ionomycin stimulation, a minimum reaction of R (Rmin) obtained by 5 $\mu$M ionomycin+1 mM EGTA stimulation, a fluorescence efficiency ($Sb_2$) of a calcium binding dye at an excitation wave length of 380 nm/500 nm and a fluorescence efficiency ($Sf_2$) of a calcium dissociation dye at an excitation wave length of 380 nm/500 nm.

Calculation formula: Intracellular calcium concentration $$(nM) = 224 \times [(R-Rmin)/(Rmax-R)] \times [Sf_2/Sb_2]$$

Using the thus calculated intracellular calcium concentration in the presence of a predetermined concentration of each of the drugs and that of the control solvent, a ratio of inhibiting calcium influx (CRACC inhibition) was obtained to calculate its concentration to inhibit 50% of CRACC ($IC_{50}$ value).

(2) Selectivity of CRACC inhibition against VOCC

A suspension of rat neuroblasts PC12-h5 ($2 \times 10^6$/ml) loaded with a calcium indicator fluorescence dye fura-2 (1 $\mu$M) was dispensed in 100 $\mu$l portions into wells of a 96 well microplate. Intracellular calcium increase stimulated with high concentration potassium chloride was induced by adding to each well a 100 $\mu$l of Hanks' balanced salt solution containing a drug to be tested in two times higher concentration than the final concentration and 100 mM of KCl (final concentration, 50 mM), and, after 30 minutes of the addition, a fluorescence intensity ratio (R) was calculated from two fluorescence intensities obtained at excitation wave lengths of 340 nm/500 nm and 380 nm/500 nm, respectively. In calculating R, self-fluorescence of the drug to be tested was measured in a cell-free system, and the effect of the self-fluorescence on the fura-2 fluorescence was corrected.

The $IC_{50}$ value of VOCC inhibition was calculated in the same manner as the case of the aforementioned CRACC inhibition, and compared with that of CRACC inhibition.

The CRACC inhibition activity ($IC_{50}$ value) of the novel compounds of Examples 1, 5, 32, 36, 38, 50, 53 and 72 and the known compounds A and D (both purchased from MYBRIDGE) was within the range of from 0.51 to 0.050 $\mu$M. In addition, the CRACC inhibition activity of these compounds was superior to the VOCC inhibition activity by a factor of from 16 to 200, thus showing selectivity.

(3) Inhibitory effect on IL-2 production

Inhibitory effect of the invention compound on IL-2 production from Jurkat cells was tested in accordance with the method described by S. Clare Chung et al. in *Br. J. Pharmacol.*, 113: 861–868, 1994, and its IC50 value was calculated.

Compounds of the Examples 1, 5, 32, 36, 38, 50, 53 and 72 and Compounds A and D showed $IC_{50}$ values of 1 $\mu$M or less.

(4) Effect on TNCB-induced contact hypersensitivity model

In five-week-old male ICR mice (SLC), effect of the invention compound on TNCB-induced contact hypersensitivity was tested in almost the same manner as the method described in Current Protocols in Immunology (John Wiley & Sons, Inc., 1994). Compounds of this invention inhibited TNCB-induced contact hypersensitivity in a dose-dependent manner.

(5) Inhibitory effect on concanavalin A (ConA)-induced hepatitis in mice

In four to five-week-old female Balb/c mice (SLC), this test was carried out by employing a method similar to the method reported by G. Tiegs et al. in *J. Clin. Invest.*, 90: 196–203 (1992). Compounds of this invention inhibited ConA-induced hepatitis in a dose-dependent manner.

(6) Inhibitory effect on collagen-induced arthritis in mice

In five-week-old male DBA/1J mice (Charles River Japan), inhibitory effect on arthritis was tested in the similar manner as the methods reported by Fumio Nishikaku and Yoshihiko Koga in *Immunopharmacology*, 25, 65–74 (1993) and by Fuminori Kato, Masanao Nomura and Kyoko Nakamura in *Annals of the Rheumatic Disease*, 55, 535–539 (1996). Compounds of this invention showed significant inhibition on arthritis.

(7) Inhibitory effect on antigen-induced airway eosinophilia in rat

In four-week-old male BN rats (Charles River, Japan), inhibitory effect on antigen-induced airway eosinophilia was tested in almost the same manner as the method reported by W. Elwood el al. in *Inflamm. Res.*, 44: 83–86 (1995). In this connection, the drug was administered 30 minutes before the antigen exposure in the case of intravenous injection or 1 hour before and 3 hours after the antigen exposure in the case of oral administration.

In this model, compounds of this invention inhibited numbers of infiltrated total leukocytes and that of infiltrated eosinophils into airways.

A pharmaceutical composition which contains the compound (I') of the present invention or a salt thereof and a pharmaceutically acceptable carrier can be prepared by a usually used method using at least one of compounds represented by the general formula (I') or salts thereof and a carrier for medicinal use, a filler and other additives usually used in pharmaceutical preparations. Its administration may be effected either by oral administration in the form of tablets, pills, capsules, granules, powders, solutions and the like or by parenteral administration in the form of intravenous, intramuscular and the like injections, suppositories, percutaneous absorption preparations and the like.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium silicate. By the usual procedures, the composition may contain other additives than the inert diluent, such as a lubricant (e.g., magnesium stearate or the like), a disintegrating agent (e.g., calcium cellulose glycolate or the like), a stabilizing agent (e.g., lactose or the like) and a solubilization assisting agent (e.g., glutamic acid, aspartic acid or the like). If necessary, tablets or pills may be coated with films of a sugar or a gastric or enteric substance such as sucrose, gelatin, hydroxypropylcellulose, hydroxypropylmethylcellulose phthalate or the like.

The liquid composition for oral administration use includes pharmaceutically acceptable emulsions, solutions, suspensions, syrups, elixirs and the like and contains a generally used inert diluent such as purified water or ethanol. In addition to the inert diluent, this composition may also contain auxiliary agents such as a moistening agent, a suspending agent and the like, as well as sweeteners, flavors, aromatics and antiseptics.

The injections for parenteral administration use include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oil (e.g., olive oil or the like), alcohol (e.g., ethanol and the like), and polysorbate 80. Such a composition may further contain auxiliary agents such as an antiseptic, a moistening agent, an emulsifying agent, a dispersing agent, a stabilizing agent (lactose for example) and a solubilization assisting agent (glutamic acid or aspartic acid for example). These compositions are sterilized by filtration through a bacteria retaining filter, blending of a germicide or irradiation. Alternatively, they may be used by firstly making into sterile solid compositions and then dissolving them in sterile water or a sterile solvent for injection use prior to their use.

In the case of oral administration, suitable daily dose is usually from about 0.001 to 10 mg/kg body weight, and the daily dose is administered once a day or divided into 2 to 4 doses per day. In the case of intravenous injection, suitable daily dose is usually from about 0.0001 to 1 mg/kg body weight, and the daily dose is administered once per several days, or once a day or divided into a plurality of doses per day. The dose is optionally decided by taking into consideration symptoms, age, sex and the like of each patient to be treated.

BEST MODE FOR CARRYING OUT THE INVENTION

The following describes the present invention further in detail based on Examples. Compounds of the present invention are not limited to the compounds described in the following Examples. In this connection, methods for the production of the starting material compounds to be used in the Examples are described as Reference Examples.

REFERENCE EXAMPLE 1

Sodium methoxide was added to a mixture of 2-acetylthiazole and methanol under ice-cooling, followed by stirring at room temperature for 20 minutes. Ethyl trifluoroacetate was added to the reaction solution under ice-cooling. After stirring for 19 hours while heating under reflux, it was purified in the usual way. Then, methyl hydrazine, acetic acid and ethanol were added thereto. After stirring for 30 minutes while heating under reflux, it was subjected to purification in the usual way to give 2-(1-methyl-3-trifluoromethyl-1H-pyrazol-5-yl)thiazole.

REFERENCE EXAMPLE 2

An n-butyl lithium-n-hexane solution (1.6 M) was added to a mixture of diisopropylamine and THF at −30° C. or below, followed by stirring at −30 to −50° C. for 15 minutes. Then, 2-propionylthiophene was added to the reaction solution at −60° C. or below, followed by stirring at −60° C. or below for 90 minutes. The reaction solution was added to a mixture of trifluoroacetic anhydride and THF, which was cooled at −60° C. After stirring at −60° C. for 1 hour, it was subjected to purification in the usual way to give a brown oil. Hydrazine hydrochloride and ethanol were added to this brown oil. After stirring at 50° C. for 2 hours, it was subjected to purification in the usual way to give 4-methyl-3-(2-thienyl)-5-trifluoromethyl-1H-pyrazole as a brown solid.

REFERENCE EXAMPLE 3

An n-butyl lithium-n-hexane solution (1.6 M) was added to a mixture of 3-(2-thienyl)-5-trifluoromethyl-1H-pyrazole and THF at −60° C. or below, followed by stirring at 0° C. for 50 minutes. Ethyl chloroformate was added to the reaction solution at −60° C. or below. After stirring at −78° C. for 1 hour, it was subjected to purification in the usual way to give a mixture of ethyl 5-(1-ethoxycarbonyl-5-trifluoromethyl-1H-pyrazol-3-yl)thiophene-2-carboxylate and ethyl 5-(1-ethoxycarbonyl-3-trifluoromethyl-1H-pyrazol-5-yl)thiophene-2-carboxylate as a light yellow solid. Then, a mixture of this mixture with sodium bicarbonate, ethanol, 1,4-dioxane and water was stirred at room temperature for 3 days, and it was subjected to purification in the usual way to give ethyl 5-(5-trifluoromethyl-1H-pyrazol-3-yl)thiophene-2-carboxylate as colorless powder crystals. This was hydrolyzed with a base in the usual way to give 5-(5-trifluoromethyl-1H-pyrazol-3-yl)thiophene-2-carboxylic acid.

REFERENCE EXAMPLE 4

An n-butyl lithium-n-hexane solution (1.6 M) was added to a mixture of 2-(1-methyl-3-trifluoromethyl-1H-pyrazol-5-yl)thiazole and THF at −50° C. or below, followed by stirring at −50° C. or below for 90 minutes. Ethyl chloroformate was added to the reaction solution at −20° C. or below. After stirring at −20° C. or below for 15 minutes, it was subjected to purification in the usual way to give ethyl 2-(1-methyl-3-trifluoromethyl-1H-pyrazol-5-yl)thiazole-5-carboxylate. This was hydrolyzed with a base in the usual way to give 2-(1-methyl-3-trifluoromethyl-1H-pyrazol-5-yl)thiazole-5-carboxylic acid.

REFERENCE EXAMPLE 5

A mixture of ethyl 5-(5-trifluoromethyl-1H-pyrazol-3-yl)thiophene-2-carboxylate, ethyl iodide, potassium carbonate and DMF was stirred at room temperature for 9 hours. The residue obtained by a usual treatment was eluted by silica gel chromatography (eluent; n-hexane:ethyl acetate=15:1) to give ethyl 5-(1-ethyl-5-trifluoromethyl-1H-pyrazol-3-yl) thiophene-2-carboxylate as colorless needle crystals. Also, by changing the eluent of the silica gel chromatography to n-hexane:ethyl acetate=10:1, ethyl 5-(1-ethyl-3-trifluoromethyl-1H-pyrazol-5-yl)thiophene-2-carboxylate was obtained as a light yellow oil. By hydrolyzing these compounds with a base in the usual way, a) 5-(1-ethyl-5-trifluoromethyl-1H-pyrazol-3-yl)thiophene-2-carboxylic acid and b) 5-(1-ethyl-3-trifluoromethyl-1H-pyrazol-5-yl) thiophene-2-carboxylic acid were obtained.

REFERENCE EXAMPLE 6 a) 5-(1-Isopropyl-5-trifluoromethyl-1H-pyrazol-3-yl) thiophene-2-carboxylic acid and b) 5-(1-isopropyl-3-trifluoromethyl-1H-pyrazol-5-yl)thiophene-2-carboxylic acid were obtained in the same manner as described in Reference Example 5.

REFERENCE EXAMPLE 7

4-Methyl-3-(2-thienyl)-5-trifluoromethyl-1H-pyrazole was allowed to react with an n-butyl lithium-n-hexane solution (1.6 M). Further, ethyl chloroformate was added at −50° C. or below. After stirring at −50° C. or below for 30 minutes, it was subjected to purification in the usual way to give a yellow oil. By hydrolyzing this in the usual way, 5-(4-methyl-5-trifluoromethyl-1H-pyrazol-3-yl)thiophene-2-carboxylic acid was obtained as colorless powder crystals.

REFERENCE EXAMPLE 8

A mixture of 5-(1-methyl-3-trifluoromethyl-1H-pyrazol-5-yl)thiophene-2-carboxylic acid, oxalyl chloride, DMF and DCE was stirred at room temperature for 90 minutes and then treated in the usual way to give 5-(1-methyl-3-trifluoromethyl-1H-pyrazol-5-yl)thiophene-2-carbonyl chloride as a brown solid.

REFERENCE EXAMPLE 9

A mixture of 5-(1-methyl-3-trifluoromethyl-1H-pyrazol-5-yl)thiophene-2-carboxylic acid, diphenylphosphoryl azide, triethylamine and toluene was stirred at 50° C. for 30 minutes. Then, tert-butanol was added to the reaction solution. After stirring at 80° C. for 5 hours, it was subjected to purification in the usual way to give tert-butyl 5-(1-methyl-3-trifluoromethyl-1H-pyrazol-5-yl)thiophene-2-carbamate as light yellow crystals.

REFERENCE EXAMPLE 10

A mixture of tert-butyl 5-(1-methyl-3-trifluoromethyl-1H-pyrazol-5-yl)thiophene-2-carbamate, trifluoroacetic acid and dichloromethane was stirred at room temperature for 2 days and then subjected to purification and salt formation in the usual way to give 5-(5-amino-2-thienyl)-1-methyl-3-trifluoromethyl-1H-pyrazole hydrochloride as light yellow powder crystals.

REFERENCE EXAMPLE 11

Zinc powder and ammonium chloride were added to an aqueous ethanol solution of 1-(4-nitrophenyl)-3,5-bis (trifluoromethyl)-1H-pyrazole under ice-cooling, followed by stirring at 20° C. or below for 30 minutes. The insoluble matter in the reaction solution was removed by celite filtration, and then the filtrate was treated in the usual way to give 1-(4-hydroxyaminophenyl)-3,5-bis(trifluoromethyl)-1H-pyrazole as a colorless solid.

REFERENCE EXAMPLE 12

A mixture of 5 N sodium hydroxide aqueous solution and ethanol was added to a mixture of 5-(1-methyl-5-trifluoromethyl-1H-pyrazol-3-yl)thiophene-2-carboxy aldehyde, silver nitrate powder and ethanol under ice-cooling. After stirring at room temperature for 1 hour, it was subjected to purification in the usual way to give 5-(1-methyl-5-trifluoromethyl-1H-pyrazol-3-yl)thiophene-2-carboxylic acid as colorless powder.

EXAMPLE 1

A mixture of 4-methylthiazole-5-carboxylic acid (108 mg), 4-[3,5-bis(trifluoromethyl)-1H-pyrazol-1-yl]aniline (223 mg), WSCD hydrochloride (152 mg) and DCE (5 ml) was stirred overnight at room temperature. Water (10 ml) was added to the reaction mixture, and the thus formed product was extracted with a mixed solvent of diethyl ether (5 ml) and ethyl acetate (10 ml). The extract was washed with 1 N hydrochloric acid, saturated sodium hydrogencarbonate aqueous solution and saturated brine in that order. The resulting organic layer was dried over anhydrous magnesium sulfate and then concentrated under a reduced pressure. The thus obtained residue was purified by silica bel column chromatography (eluent; n-hexane:ethyl acetate=3:1–2:1) and then recrystallized from a mixed solvent of ethyl acetate and n-hexane to give 4-methyl-4'-[3,5-bis(triflurormethyl)-1H-pyrazol-1-yl]thiazole-5-carboxyanilide (143 mg) as colorless needles.

EXAMPLE 2

4-Chlorobenzol chloride (88 mg) and THF (2 ml) were added to a mixture of 4-[3,5-bis(trifluromethyl)-1H-pyrazol-1-yl]aniline (150 mg), triethylamine (57 mg) and THF (2 ml) under ice-cooling, followed by stirring at room temperature for 4 hours. Water was added to the reaction solution, the thus formed product was extracted with ethyl acetate and then the extract was washed with 1 N hydrochloric acid aqueous solution, saturated sodium bicarbonate aqueous solution and saturated brine in that order. The organic layer was dried over anhydrous magnesium sulfate and then concentrated under a reduced pressure. By recrystallizing the resulting residue from a mixed solvent of ethyl acetate and n-hexane, 4-chloro-4'-[3,5-bis(trifluoromethyl)-1H-pyrazol-1-yl]benzanilide (105 mg) was obtained as colorless powder crystals.

EXAMPLE 3

A mixture of 4'-chloro-5-(4-methyl-5-trifluoromethyl-1H-pyrazol-3-yl)thiophene-2-carboxyanilide (360 mg), methyl iodide (199 mg), potassium carbonate (129 mg) and DMF (5 ml) was stirred at room temperature for 3 days. Water (10 ml) was added to the reaction solution, the thus formed product was extracted with ethyl acetate and then the extract was washed with saturated brine. The organic layer was dried over anhydrous magnesium sulfate and then concentrated under a reduced pressure. The resulting residue was purified by silica gel column chromatography (eluent; n-hexane:ethyl acetate 9:1–4:1) and then recrystallized from a mixed solvent of ethyl acetate and n-hexane to give 4'-chloro-5-(1,4-dimethyl-5-trifluoromethyl-1H-pyrazol-3-yl)thiophene-2-carboxyanilide (13 mg) as colorless powder crystals.

EXAMPLE 4

In the silica gel column chromatography treatment of Example 3, a compound eluted after the compound of Example 3 was recrystallized from a mixed solvent of ethyl acetate and hexane to give 4'-chloro-5-(1,4-dimethyl-3-trifluoromethyl-1H-pyrazol-5-yl)thiophene-2-carboxyanilide (86 mg) as colorless powder crystals.

EXAMPLE 5

A mixture of 5-(1-methyl-3-trifluoromethyl-1H-pyrazol-5-yl)thiophene-2-carbonyl chloride (150 mg) and dichloromethane (1.5 ml) was added under ice-cooling to a mixture of 2-chloroaniline (68 mg), pyridine (42 mg) and dichloromethane (2 ml), followed by stirring for 30 minutes at room temperature. Saturated sodium hydrogencarbonate aqueous solution was added to the reaction mixture, the thus formed product was extracted with ethyl acetate and then the extract was washed with saturated brine. The resulting organic layer was dried over anhydrous magnesium sulfate and then concentrated under a reduced pressure. The resulting residue was recrystallized from ethanol to give 2'-chloro-5-(1-methyl-3-trifluoromethyl-1H-pyrazol-5-yl)thiophene-2-carboxyanilide (80 mg) as colorless crystals.

EXAMPLE 6

5-(1-Methyl-3-trifluoromethyl-1H-pyrazol-5-yl)thiophene-2-carbonyl chloride (295 mg) and THF (3 ml) were added to a mixture of 2-amino-1-methylpyrrole hydrochloride (202 mg), potassium carbonate (553 mg), THF (2 ml) and water (4 ml), followed by stirring at room temperature for 30 minutes. Water was added to the reaction solution, the thus formed product was extracted with ethyl acetate and then the extract was washed with 1 N hydrochloric acid, saturated sodium bicarbonate aqueous solution and water in that order. The organic layer was dried over anhydrous magnesium sulfate and then concentrated under a reduced pressure. The resulting residue was purified by silica gel column chromatography (eluent; n-hexane:ethyl acetate=2:1–3:2) and then recrystallized from a mixed solvent of ethyl acetate and n-hexane to give N-(1-methyl-2-pyrrolyl)-5-(1-methyl-3-trifluoromethyl-1H-pyrazol-5-yl)thiophene-2-carboxamide (126 mg) as light yellow powder crystals.

EXAMPLE 7

5-(1-Methyl-3-trifluoromethyl-1H-pyrazol-5-yl)thiophene-2-carbonyl chloride (150 mg) and THF (2 ml) were added to a mixture of 70% ethylamine aqueous solution (1 ml) and THF (2 ml), followed by stirring at room temperature for 2 hours. Water was added to the reaction solution, the thus formed product was extracted with ethyl acetate and then the extract was washed with saturated brine. The organic layer was dried over anhydrous magnesium sulfate and then concentrated under a reduced pressure. The resulting residue was recrystallized from a mixed solvent of ethyl acetate and n-hexane to give N-ethyl-5-(1-methyl-3-trifluoromethyl-1H-pyrazol-5-yl)thiophene-2-carboxamide (96 mg) as colorless powder crystals.

EXAMPLE 8

5-(1-Methyl-5-trifluoromethyl-1H-pyrazol-3-yl)thiophene-2-carbonyl chloride (100 mg) and dichloromethane (2 ml) were added to a mixture of 2-aminothiazole (68 mg), saturated sodium bicarbonate aqueous solution (1 ml) and dichloromethane (1 ml), followed by stirring at room temperature for 5 hours. Water was added to the reaction solution, the thus formed product was extracted with ethyl acetate and then the extract was washed with saturated brine. The organic layer was dried over anhydrous magnesium sulfate and then concentrated under a reduced pressure. The resulting residue was purified by silica gel column chromatography (eluent; n-hexane:ethyl acetate=4:1–2:1) and then washed with diethyl ether to give 5-(1-methyl-5-trifluoromethyl-1H-pyrazol-3-yl)-N-(2-thiazolyl)thiophene-2-carboxamide (68 mg) as colorless solid.

EXAMPLE 9

Sodium methoxide (257 mg) was added to a mixture of 3'-acetyl-4-chlorobenzanilide (1.00 g) and methanol (10 ml) under ice-cooling, followed by stirring at room temperature for 2 hours. Ethyl trifluoroacetate (0.522 ml) was added to the reaction solution under ice-cooling, followed by stirring under heat reflux for 3 days. Water (50 ml) was added to the reaction mixture, the thus formed product was extracted with ethyl acetate and then the extract was washed with saturated brine. The organic layer was dried over anhydrous sodium sulfate and then concentrated under a reduced pressure. The resulting residue was purified by silica gel column chromatography (eluent; n-hexane:ethyl acetate=2:1–1:1) to give a light yellow oil. A mixture of this oil with methyl hydrazine (0.122 ml), acetic acid (1 ml) and ethanol (10 ml) was stirred under heat reflux for 15 hours. After spontaneous cooling, the reaction solution was concentrated under a reduced pressure. After adding ethyl acetate, the thus obtained residue was washed with saturated sodium bicarbonate aqueous solution and saturated brine in that order. The organic layer was dried over anhydrous sodium sulfate and then concentrated under a reduced pressure. The resulting residue was purified by silica gel column chromatography (eluent; n-hexane:ethyl acetate=6:1) and then recrystallized from a mixed solvent of ethyl acetate and n-hexane to give 4-chloro-3'-(1-methyl-5-trifluoromethyl-1H-pyrazol-3-yl)benzanilide (60 mg) as colorless powder crystals.

EXAMPLE 10

In the silica gel column chromatography treatment of Example 9, a compound eluted after the compound of Example 9 was recrystallized from a mixed solvent of ethyl acetate and hexane to give 4-chloro-3'-(1-methyl-3-trifluoromethyl-1H-pyrazol-5-yl)benzanilide (134 mg) as colorless powder crystals.

EXAMPLE 11

Sodium triacetoxyborohydride (530 mg) was added to a mixture of 5-(1-methyl-5-trifluoromethyl-1H-pyrazol-3-yl)thiophene-2-carboxy aldehyde (260 mg), 4-chloroaniline (134 mg), acetic acid (0.1 ml) and dichloromethane (3 ml), followed by stirring at room temperature for 2 hours and 20 minutes. Saturated sodium bicarbonate aqueous solution (10 ml) was added to the reaction solution, the thus formed product was extracted with ethyl acetate and then the extract was washed with saturated brine. The organic layer was dried over anhydrous magnesium sulfate and then concentrated under a reduced pressure. The resulting residue was purified by silica gel column chromatography (eluent; n-hexane:ethyl acetate=10:1–6:1) to give 3-[5-[(4-chloroanilino)methyl]-2-thienyl]-1-methyl-5-trifluoromethyl-1H-pyrazole (313 mg) as a colorless solid.

EXAMPLE 12

A mixture of ethyl 1-[4-(4-chlorobenzoylamino) phenyl]-trifluoromethyl-1H-pyrazope-4-carboxylate (150 mg), 1 N sodium hydroxide aqueous solution (1 ml) and ethanol (2 ml) was stirred at 45° C. for 4 hours. After spontaneous cooling, 1 N hydrochloric acid aqueous solution (2 ml) was added to the reaction solution, the thus formed product was extracted with ethyl acetate and then the extract was washed with saturated brine. The organic layer was dried over anhydrous magnesium sulfate and then concentrated under a reduced pressure. The resulting residue was recrystallized from ethanol to give 1-[4-(4-chlorobenzoylamino)phenyl]-5-trifluoromethyl-1H-pyrazole-4-carboxylic acid (91 mg) as colorless powder crystals.

EXAMPLE 13

A mixture of 1-tert-butoxycarbonylpiperidine-4-carboxylic acid (198 mg), 4-[3,5-bis(trifluoromethyl)-1H-pyrazol-1-yl)aniline (206 mg), WSCD hydrochloride (172 mg) and THF (3 ml) was stirred overnight at room temperature. After adding ethyl acetate, the reaction solution was washed with water, saturated sodium bicarbonate aqueous solution, 1 N hydrochloric acid and saturated brine in that order. The organic layer was dried over anhydrous sodium sulfate and then concentrated under a reduced pressure. The resulting residue was purified by silica gel column chromatography (eluent; n-hexane:ethyl acetate=7:1–5:1) to give tert-butyl 4-[4-[3,5-bis(trifluoromethyl)-1H-pyrazol-1-yl]phenylaminocarbonyl]piperidine-1-carboxylate (279 mg) as a colorless amorphous solid. 4 N Hydrochloric acid ethyl acetate solution (2.60 ml) was added to a mixture of this solid (263 mg) and ethyl acetate (2.6 ml), followed by stirring at room temperature for 2 hours and 45 minutes. The reaction solution was concentrated under a reduced pressure, diethyl ether was added to the thus obtained residue, and the mixture was concentrated under a reduced pressure. By recrystallizing the resulting residue from a mixed solvent of ethyl acetate and n-hexane, [4'-[3,5-bis(trifluoromethyl)-1H-pyrazol-1-yl]piperidine-4-carboxyanilide hydrochloride (201 mg) was obtained as colorless powder crystals.

EXAMPLE 14

Methanesulfonyl chloride (80 mg) was added to a mixture of ethyl 1-(4-aminophenyl)-5-trifluoromethyl-1H-pyrazole-4-carboxylate (150 mg), triethylamine (76 mg) and THF (2 ml) under ice-cooling, followed by stirring at room temperature for 4 hours. Thereafter, the same treatment of Example 2 was carried out to give ethyl 1-(4-methanesulfonylaminophenyl)-5-trifluoromethyl-1H-pyrazole-4-carboxylate (29 mg) as a colorless solid.

EXAMPLE 15

To a mixture of 5-(1-methyl-3-trifluoromethyl-1H-pyrazol-5-yl)thiophene-2-carboxy aldehyde (583 mg), diethyl 4-chloro-α-fluorobenzylphosphonate (755 mg) and THF (8 ml) was added at −60° C. lithium diisopropylamide prepared from diisopropylamine (259 mg) and an n-butyl lithium-n-hexane solution (1.6 N, 1.6 ml), followed by stirring for 6 hours and 30 minutes while gradually warming it to room temperature. Water (10 ml) was added to the reaction solution, the thus formed product was extracted with ethyl acetate and then the extract was washed with saturated brine. The organic layer was dried over anhydrous magnesium sulfate and then concentrated under a reduced pressure. The resulting residue was purified by silica gel column chromatography (eluent; n-hexane:ethyl acetate= 16:1–8:1) to give 5-[5-[(E)-2-(4-chlorophenyl)-2-fluorovinyl]-2-thienyl]-1-methyl-3-trifluoromethyl-1H-pyrazole (32 mg) as an yellow oil.

EXAMPLE 16

4-Chlorophenyl isocyanate (461 mg) was added to a mixture of 4-(1-methyl-3-trifluoromethyl-1H-pyrazol-5-yl) piperidine (540 mg) and THF (5 ml) under ice-cooling, followed by stirring overnight at room temperature. Water (10 ml) was added to the reaction solution, the thus formed product was extracted with ethyl acetate and then the extract was washed with saturated brine. The organic layer was dried over anhydrous magnesium sulfate and then concentrated under a reduced pressure. A mixed solvent of acetone and diethyl ether was added to the thus obtained residue, the insoluble matter was removed by filtration and then the filtrate was concentrated under a reduced pressure. The resulting residue was purified by silica gel column chromatography (eluent; n-hexane:ethyl acetate=1:1) and then recrystallized from a mixed solvent of ethyl acetate and n-hexane to give 4'-chloro-4-(1-methyl-3-trifluoromethyl-1H-pyrazol-5-yl)piperidine-1-carboxyanilide (391 mg) as colorless powder crystals.

EXAMPLE 17

A mixture of 1-trityl-1H-imidazole-4-carboxylic acid (300 mg), 4-[3,5-bis(trifluoromethyl)-1H-pyrazol-1-yl) aniline (200 mg), WSCD hydrochloride (162 mg), DMF (0.5 ml) and THF (4 ml) was stirred overnight at room temperature. Water (10 ml) was added to the reaction solution, the thus formed product was extracted with ethyl acetate and then the extract was washed with saturated brine. The organic layer was dried over anhydrous magnesium sulfate and then concentrated under a reduced pressure. The resulting residue was purified by silica gel column chromatography (eluent; n-hexane:ethyl acetate=3:1). Then, concentrated hydrochloric acid (0.1 ml) and acetone (3 ml) were added, followed by stirring overnight at room temperature. The reaction solution was concentrated under a reduced pressure, diethyl ether was added to the thus obtained residue, and then the mixture was concentrated under a reduced pressure. A mixed solvent of ethanol and diethyl ether was added to the thus obtained residue, the insoluble matter was removed by filtration and then the filtrate was concentrated under a reduced pressure. The resulting residue was purified by silica gel column chromatography (eluent; n-hexane:ethyl acetate=1:1–2:3) and then recrystallized from a mixed solvent of ethyl acetate and n-hexane, thereby obtaining [4'-[3,5-bis(trifluoromethyl)-1H-pyrazol-1-yl]-1H-imidazole-4-carboxyanilide (35 mg) as colorless powder crystals.

Other compounds of Examples shown in the following Tables 2 and 3 were obtained in the same manner as described in the aforementioned Examples. Structural formulae and physicochemical properties of the compounds of reference examples are shown in the following Table 1, and structural formulae and physicochemical properties of the compounds of Examples are shown in Tables 2 and 3. In this connection, compounds having the chemical structures shown in Tables 4 and 5 can be produced easily in almost the same manner as the methods described in the aforementioned Examples or production methods, or by applying thereto slight modifications self-evident to those skilled in the art.

Abbreviations in the tables are Rex: Reference Example; Ex: Example; Co: compound number; Sy: production method (each numeral shows corresponding number of the aforementioned Example, indicating that the compound was produced by the same manner of the aforementioned Example); Str: structural formula; Dat: physicochemical properties (F: FAB-MS (M+H)$^+$; FN: FAB-MS (M−H)$^−$; E: EI-MS; M: melting point [°C.]; (d): decomposition; N1: characteristic peak δ ppm of NMR (DMSO-d$_6$, TMS internal standard); N2: characteristic peak δ ppm of NMR (CDCl$_3$, TMS internal standard); and *: absence of the group.

TABLE 1

| Rfx | Str | Dat |
|---|---|---|
| 1 | 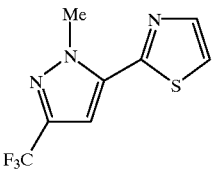 | N2: 4.32(3H, s), 6.90(1H, s), 7.45(1H, d, J=3.3Hz), 7.93(1H, d, J=3.0Hz) |
| 2 | 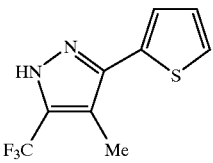 | N2: 2.29(3H, s), 7.16(1H, dd, J=5.2, 3.7Hz), 7.25(1H, dd, J=4.0, 1.0Hz), 7.44(1H, dd, J=5.4, 1.0Hz), 10.86(1H, brs) |
| 3 | 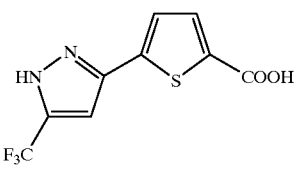 | N1: 7.07(1H, s), 7.60(1H, d, J=3.7Hz), 7.76(1H, d, J=3.7Hz), 14.42(1H, brs) |

TABLE 1-continued

| Rfx | Str | Dat |
|---|---|---|
| 4 | (1-Me, 3-CF3 pyrazol-5-yl)-thiazole-5-COOH | N1: 4.26(3H, s), 7.56(1H, s), 8.52(1H, s) |
| 5a) | (1-Et, 5-CF3 pyrazol-3-yl)-thiophene-2-COOH | N1: 1.42(3H, t, J=7.1Hz), 4.30(2H, q, J=7.2Hz), 7.46(1H, s), 7.58(1H, d, J=3.9Hz), 7.71(1H, d, J=3.6Hz), 13.18(1H, brs) |
| 5b) | (1-Et, 3-CF3 pyrazol-5-yl)-thiophene-2-COOH | N1: 1.39(3H, t, J=7.2Hz), 4.37(2H, q, J=7.2Hz), 7.15(1H, s), 7.53(1H, d, J=3.9Hz), 7.80(1H, d, J=3.9Hz), 13.46(1H,brs) |
| 6a) | (1-iPr, 5-CF3 pyrazol-3-yl)-thiophene-2-COOH | N1: 1.49(6H, d, J=6.8Hz), 4.57–4.68(1H, m), 7.32(1H, s), 7.47(1H,d,J=3.9Hz), 7.50(1H,d,J=3.9Hz) |
| 6b) | (1-iPr, 3-CF3 pyrazol-5-yl)-thiophene-2-COOH | N1: 1.44(6H, d, J=6.9Hz), 4.77–4.88(1H, m), 7.08(1H, s), 7.48(1H, d, J=3.9Hz), 7.80(1H, d, J=3.6Hz) |
| 7 | (3-CF3, 4-Me pyrazol-5-yl)-thiophene-2-COOH | N1: 2.28(3H, s), 7.53(1H, d, J=3.9Hz), 7.81(1H, d, J=3.9Hz), 13.53(1H, brs), 14.11(1H, brs) |
| 8 | (1-Me, 3-CF3 pyrazol-5-yl)-thiophene-2-COCl | N2: 4.09(3H, s), 6.78(1H, s), 7.30(1H, d, J=4.4Hz), 8.00(1H, d, J=3.9Hz) |
| 9 | (1-Me, 3-CF3 pyrazol-5-yl)-thiophene-2-NH-Boc | N2: 1.54–1.56(9H+H2O, m), 4.00(3H, s), 6.50(1H, d, J=3.6Hz), 6.57(1H, s), 6.91(1H, d, J=3.9Hz) |

TABLE 1-continued
| Rfx | Str | Dat |
|---|---|---|
| 10 | 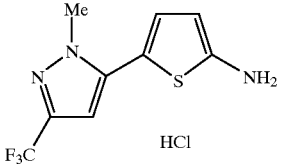 | N1: 3.96(3H, s), 6.29(1H, d, J=3.9Hz), 6.77(1H, s), 7.09(1H, d, J=3.9Hz), 7.1 (br) |
| 11 | 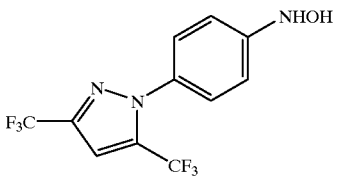 | F: 312 |
| 12 | 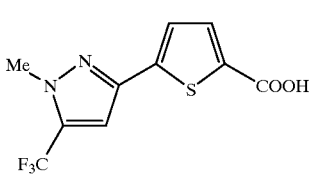 | F: 277 |
TABLE 2
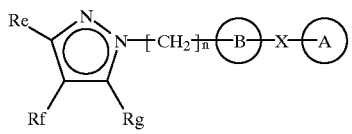
(Ia)
| Ex | Re | Rf | Rg | n | | X | A | Sy | Dat |
|---|---|---|---|---|---|---|---|---|---|
| 1 | CF$_3$ | H | CF$_3$ | 0 | (p-phenylene) | NHCO | (4-methylthiazol-5-yl) | — | M:144–145; N1:2.64 (3H, s) |
| 2 | CF$_3$ | H | CF$_3$ | 0 | (p-phenylene) | NHCO | (4-chlorophenyl) | — | M:196–197; N1:7.82 (1H, s) |
| 12 | H | COOH | CF$_3$ | 0 | (p-phenylene) | NHCO | (4-chlorophenyl) | — | M:>300 |
| 13 | CF$_3$ | H | CF$_3$ | 0 | (p-phenylene) | NHCO | (4-methylpiperidinyl·HCl) | — | F:407 |
| 14 | H | COOEt | CF$_3$ | 0 | (p-phenylene) | NHSO$_2$ | Me | — | M:156–158 |

TABLE 2-continued (Ia)

| Ex | Re | Rf | Rg | n | B | X | A | Sy | Dat |
|---|---|---|---|---|---|---|---|---|---|
| 17 | CF$_3$ | H | CF$_3$ | 0 | 1,4-phenylene | NHCO | 4-methyl-1H-imidazol-yl | — | N1:10.23(1H, s) |
| 18 | CF$_3$ | H | CF$_3$ | 0 | 1,4-phenylene | NHCO | 2-chlorophenyl | 1 | M:183–185; N1:7.82 (1H, s) |
| 19 | CF$_3$ | H | CF$_3$ | 0 | 1,4-phenylene | NHCO | thiazol-2-yl | 1 | M:174–175; N1:8.15 (1H, d, J=2.9Hz), 8.19(1H, d, J=3.4Hz) |
| 20 | CF$_3$ | H | CF$_3$ | 0 | 1,4-phenylene | N(OH)—CO | 4-methyl-1,2,3-thiadiazol-5-yl | 1 | M:126–129; N2:2.94 (3H, s), 7.10(1H, s) |
| 21 | CF$_3$ | H | CF$_3$ | 0 | 1,4-phenylene | NHCO | 4-methyl-1,2,3-thiadiazol-5-yl | 1 | M:166–168; N1:2.84 (3H, s), 7.83(1H, s) |
| 22 | Me | H | Me | 0 | 1,4-phenylene | NHCO | 4-methyl-1,2,3-thiadiazol-5-yl | 1 | M:101–103 |
| 23 | H | H | H | 0 | 1,4-phenylene | NHCO | 4-methyl-1,2,3-thiadiazol-5-yl | 1 | M:184–186 |
| 24 | H | COOEt | CF$_3$ | 0 | 1,4-phenylene | NHCO | 4-chlorophenyl | 8 | M:201–202 |
| 25 | CF$_3$ | H | CF$_3$ | 0 | 2,5-pyridinediyl | NHCO | 4-methyl-1,2,3-thiadiazol-5-yl | 1 | M:158–159 |
| 26 | H | COOEt | CF$_3$ | 0 | 1,4-phenylene | NHCO | 4-methyl-1,2,3-thiadiazol-5-yl | 1 | M:118–120 |
| 27 | CF$_3$ | H | H | 0 | 1,4-phenylene | NHCO | 4-methyl-1,2,3-thiadiazol-5-yl | 1 | M:158–161 |

TABLE 2-continued
(Ia)
| Ex | Re | Rf | Rg | n | B | X | A | Sy | Dat |
|---|---|---|---|---|---|---|---|---|---|
| 28 | CF$_3$ | H | CF$_3$ | 0 |  | NHCO |  | 1 | M:194–196 |
| 29 | H | H | CF$_3$ | 0 |  | NHCO |  | 1 | M:133–135 |
| 30 | CF$_3$ | H | CF$_3$ | 0 |  | NHCO |  | 1 | M:215–218 |
| 31 | CF$_3$ | H | CF$_3$ | 0 |  | NHCO |  | 1 | M:135–136 |
| 32 | CF$_3$ | H | CF$_3$ | 0 |  | NHCO |  | 1 | M:169–172; N1:2.48 (3H, s) |
| 33 | CF$_3$ | H | CF$_3$ | 1 |  | NHCO |  | 1 | M:125–126 |
| 34 | H | COOEt | CF$_3$ | 0 |  | NHCO |  | 1 | M:163–165 |
| 35 | H | COOEt | CF$_3$ | 0 |  | NHCO |  | 2 | M:141–143 |
| 36 | CF$_3$ | H | CF$_3$ | 0 |  | NHCO |  | 1 | M:188–190; N1:9.14 (1H, d, J=1.5Hz) |
| 37 | CF$_3$ | H | CF$_3$ | 0 |  | NHCO |  | 1 | M:188–190 |
| 38 | CF$_3$ | H | CF$_3$ | 0 |  | NHCO | | 1 | M:156; N1:3.90(3H, s) |

TABLE 2-continued
(Ia)
| Ex | Re | Rf | Rg | n | B | X | A | Sy | Dat |
|---|---|---|---|---|---|---|---|---|---|
| 39 | CF$_3$ | H | CF$_3$ | 0 | 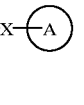 | CONH |  | 1 | F:422 |
| 40 | CF$_3$ | H | CF$_3$ | 0 | 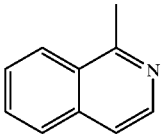 | NHCO |  | 1 | M:99–100 |
| 41 | H | COOEt | CF$_3$ | 0 | 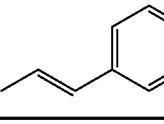 | NHCO | 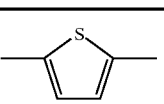 | 5 | M:176–178 |
TABLE 3
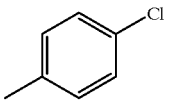
(Ib)
| Ex | Ra | Rb | Rc | Rd | n | B | X | A | Sy | Dat |
|---|---|---|---|---|---|---|---|---|---|---|
| 3 | * | Me | CF$_3$ | Me | 0 | 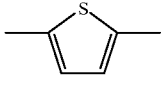 | CONH | 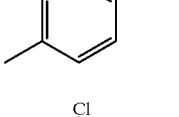 | — | M:210–213 |
| 4 | Me | * | CF$_3$ | Me | 0 | 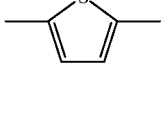 | CONH | 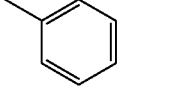 | — | M:192–196; N1:2.15 (3H, s), 3.91(3H, s) |
| 5 | Me | * | CF$_3$ | H | 0 | 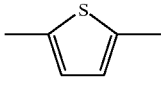 | CONH | 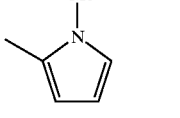 | — | M:156; N2: 4.08(3H, s), 7.13(1H, dt, J=7.8, 1.5Hz) |
| 6 | Me | * | CF$_3$ | H | 0 | 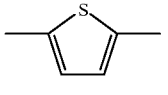 | CONH | 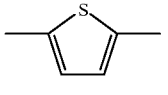 | — | M:158–159; N1:3.44 (3H, s), 4.07(3H, s) |
| 7 | Me | * | CF$_3$ | H | 0 | 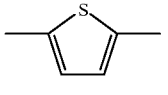 | CONH | Et | — | M:136–137 |

TABLE 3-continued
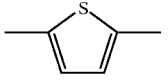
(Ib)
| Ex | Ra | Rb | Rc | Rd | n | B | X | A | Sy | Dat |
|---|---|---|---|---|---|---|---|---|---|---|
| 8 | * | Me | CF₃ | H | 0 | 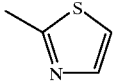 | CONH | 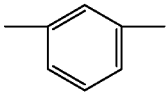 | — | M:244–246; N2:4.04 (3H, s) |
| 9 | * | Me | CF₃ | H | 0 | 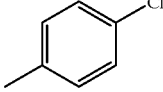 | NHCO | 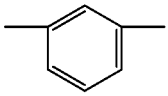 | — | M:173–175; N2:4.02 (3H, s) |
| 10 | Me | * | CF₃ | H | 0 | 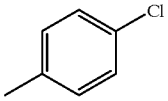 | NHCO | 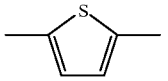 | — | M:150–153 |
| 11 | * | Me | CF₃ | H | 0 | 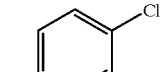 | CH₂NH | 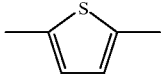 | — | M:113–115; N2:4.48 (2H, s) |
| 15 | Me | * | CF₃ | H | 0 | 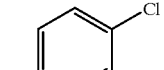 | CH=CF (cis) | 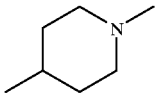 | — | E:386 |
| 16 | Me | * | CF₃ | H | 0 | 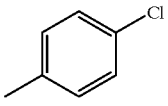 | CONH | 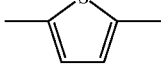 | — | M:163–165 |
| 42 | * | H | CF₃ | H | 0 | 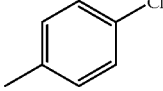 | CONH |  | 1 | M:246–247 |
| 43 | Et | * | CF₃ | H | 0 | 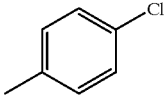 | CONH |  | 1 | M:177; N1: 1.51(3H, t, J=7.3Hz), 4.36(2H, q, J=7.3Hz) |
| 44 | * | iPr | CF₃ | H | 0 | 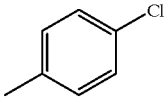 | CONH | 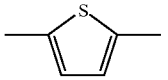 | 1 | M188–190; N1:4.59–4.70(1H, m) |
| 45 | Me | * | CF₃ | H | 0 | 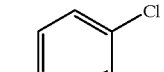 | CONH | 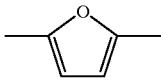 | 1 | M:204–206; N1:4.07 (3H, s) |
| 46 | Me | * | CF₃ | H | 0 | 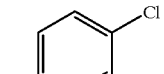 | CONH | | 1 | M:183–185; N2:4.13 (3H,s), 6.78(1H, d, J=4.0 Hz) |

TABLE 3-continued
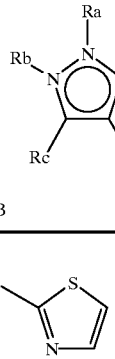
(Ib)
| Ex | Ra | Rb | Rc | Rd | n | B | X | A | Sy | Dat |
|---|---|---|---|---|---|---|---|---|---|---|
| 47 | Me | * | CF$_3$ | H | 0 | 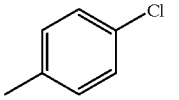 | CONH | 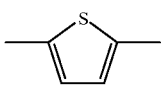 | 2 | M:163–164 |
| 48 | Me | * | CF$_3$ | H | 0 | 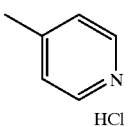 | CONH | 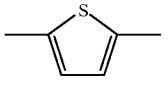 | 8 | M:247(d) |
| 49 | Me | * | CF$_3$ | H | 0 | 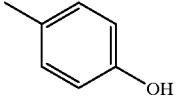 | CONH | 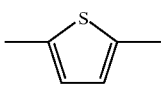 | 1 | M:185–186; N1:9.32 (1H, s), 10.17(1H, s) |
| 50 | Me | * | CF$_3$ | H | 0 | 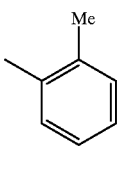 | CONH | 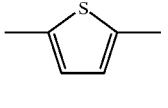 | 2 | M:159–161; N2:4.06 (3H, s) |
| 51 | Me | * | CF$_3$ | H | 0 | 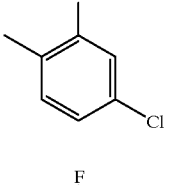 | CONH |  | 2 | M:181–183; N2:4.08 (3H, s) |
| 52 | Me | * | CF$_3$ | H | 0 | 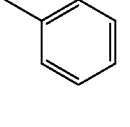 | CONH |  | 2 | M:147–148; N1:4.08 (3H, s) |
| 53 | Me | * | CF$_3$ | H | 0 | 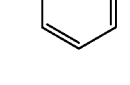 | CONH |  | 5 | M:129–130; N2:4.07 (3H, s) |
| 54 | Me | * | CF$_3$ | H | 0 | 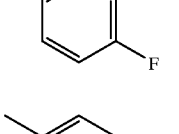 | CONH | 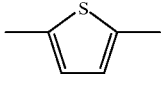 | 8 | M:189–192; N2:4.07 (3H, s) |
| 55 | Me | * | CF$_3$ | H | 0 | 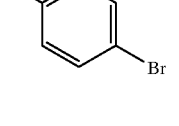 | CONH | | 8 | M:191–192; N2:4.07 (3H, s) |

TABLE 3-continued
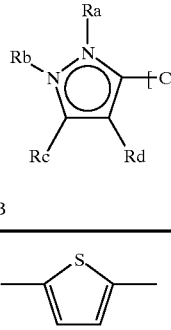
(Ib)
| Ex | Ra | Rb | Rc | Rd | n | B | X | A | Sy | Dat |
|---|---|---|---|---|---|---|---|---|---|---|
| 56 | Me | * | CF₃ | H | 0 | 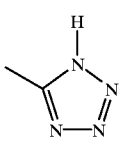 | CONH | 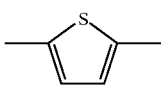 | 2 | M:285–287(d) |
| 57 | Me | * | CF₃ | H | 0 | 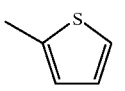 | CONH | 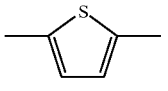 | 2 | N2:4.07(3H, s) |
| 58 | Me | * | CF₃ | H | 0 | 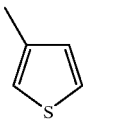 | CONH | 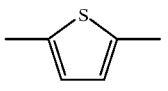 | 2 | M:166–168; N2:7.13 (1H, dd, J=4.9, 1.5Hz), 7.31(1H, dd, J=5.2, 3.2Hz), 7.68(1H, dd, J=3.0, 1.5Hz) |
| 59 | Me | * | CF₃ | H | 0 | 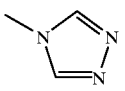 | CONH | 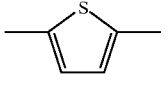 | 5 | M:207–210 |
| 60 | Me | * | CF₃ | H | 0 | 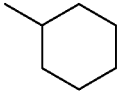 | CONH | 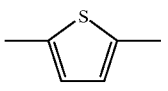 | 8 | M:140–141; N1:1.10–1.20(1H, m), 1.24–1.37 (4H, m), 1.58–1.66(1H, m), 1.69–189(4H, m) |
| 61 | * | Me | CF₃ | H | 0 | 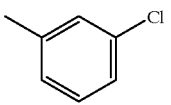 | CONH | 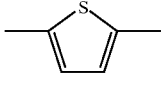 | 1 | M:156–157 |
| 62 | * | Me | CF₃ | H | 0 | 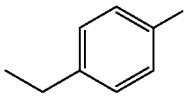 | CONH | 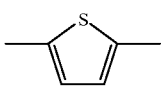 | 1 | M:197–199 |
| 63 | * | Me | CF₃ | H | 0 | 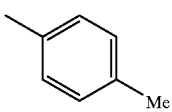 | CONH | 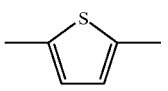 | 5 | M:205–207 |
| 64 | * | Me | CF₃ | H | 0 | 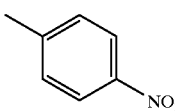 | CONH | 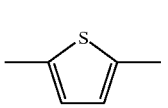 | 5 | M:234–236; N2:4.04 (3H, m) |
| 65 | * | Me | CF₃ | H | 0 | 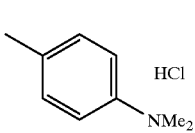 | CONH | HCl | 8 | M:230 |

TABLE 3-continued
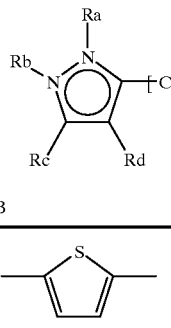
(Ib)
| Ex | Ra | Rb | Rc | Rd | n | B | X | A | Sy | Dat |
|---|---|---|---|---|---|---|---|---|---|---|
| 66 | * | Me | CF$_3$ | H | 0 | 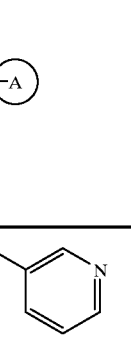 | CONH | 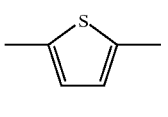 | 1 | M:195–196 |
| 67 | * | Me | CF$_3$ | H | 0 | 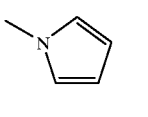 | CONH | 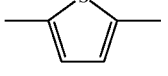 | 8 | M:211–215 |
| 68 | Me | * | CF$_3$ | H | 0 | 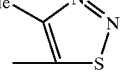 | NHCO | 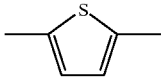 | 1 | M:148–149; N1:2.86 (3H, s) |
| 69 | Me | * | CF$_3$ | H | 0 | 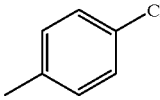 | CONMe | 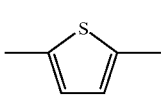 | 5 | M:136–137; N1:3.35 (3H, s) |
| 70 | * | Me | CF$_3$ | H | 0 | 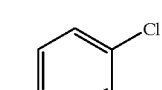 | NHCO | 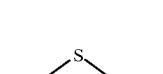 | 8 | M:197–199 |
| 71 | Me | * | CF$_3$ | H | 0 | 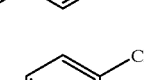 | NHCO |  | 8 | M:166–168; N1:11.92 (1H, s) |
| 72 | Me | * | CF$_3$ | H | 0 | 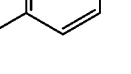 | NHCO | 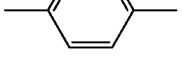 | 9 | M:187–188; N2:3.93 (3H, s) |
| 73 | Me | * | CF$_3$ | H | 0 |  | NHCO | 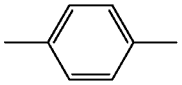 | 9 | F:368; N1:2.83(3H, s) |
| 74 | Me | * | CF$_3$ | H | 0 | 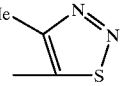 | CONH | 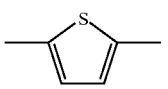 | 13 | M:265–266 |
| 75 | Me | * | Me | H | 0 | 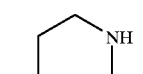 | CONH | 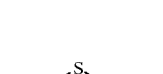 | 1 | M:198–200 |
| 76 | Me | * | H | H | 0 |  | CONH |  | 1 | M:206–208 |

TABLE 3-continued (Ib)

| Ex | Ra | Rb | Rc | Rd | n | B | X | A | Sy | Dat |
|---|---|---|---|---|---|---|---|---|---|---|
| 77 | Me | * | CF₃ | H | 0 | 3,4-dimethylthiophene | CONH | 4-Cl-phenyl | 1 | M:162–164 |
| 78 | Me | * | CF₃ | H | 0 | thiophene | CONH | 4-iPr-phenyl | 8 | M:163–164 |
| 79 | Me | * | CF₃ | H | 0 | thiophene | CONH | 4-CN-phenyl | 8 | M:211–214 |
| 80 | Me | * | CF₃ | H | 0 | thiophene | CONH | 4-NH₂-phenyl | 8 | M:181–183 |
| 81 | Me | * | CF₃ | H | 0 | thiophene | CONH | 4-OMe-phenyl | 5 | M:166–167 |
| 82 | Me | * | CF₃ | H | 0 | thiophene | CONH | 4-COOEt-phenyl | 5 | M:183–185 |
| 83 | Me | * | CF₃ | H | 1 | thiophene | CONH | 4-Cl-phenyl | 1 | M:137–139 |
| 84 | Me | * | CF₃ | H | 0 | thiophene | | 4-acetyl-3,4-dihydro-2H-benzo[1,4]oxazine | 2 | M:153–155 |

TABLE 4
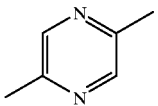
(Ia)
| Co | Re | Rf | Rg | n | B | X | A |
|---|---|---|---|---|---|---|---|
| 11 | CF$_3$ | H | CF$_3$ | 0 | 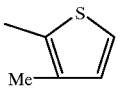 | NHCO | 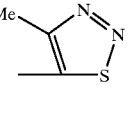 |
| 12 | CF$_3$ | H | CF$_3$ | 0 | | NHCO | 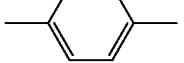 |
| 13 | CF$_3$ | H | CF$_3$ | 0 | 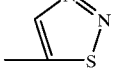 | NHCO | 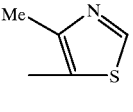 |
| 14 | CF$_3$ | H | CF$_3$ | 0 | | NHCS | 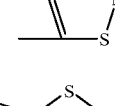 |
| 15 | CF$_3$ | H | CF$_3$ | 0 | | NHCS | 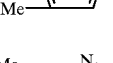 |
| 16 | CF$_3$ | H | CF$_3$ | 0 | | NHCS | 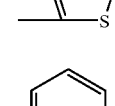 |
| 17 | CF$_2$CF$_3$ | H | CF$_2$CF$_3$ | 0 | | NHCO | 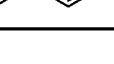 |
| 18 | CF$_2$CF$_3$ | H | CF$_2$CF$_3$ | 0 | | NHCO | 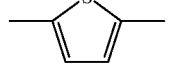 |
TABLE 5
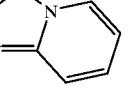
(Ib)
| Co | Ra | Rb | Rc | Rd | n | B | X | A |
|---|---|---|---|---|---|---|---|---|
| 1 * | Me | CF$_3$ | | H | 0 | (thiophene) | CONH | (imidazopyridine) |

TABLE 5-continued

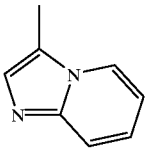

(Ib)

| Co | Ra | Rb | Rc | Rd | n | X | A |
|----|----|----|----|-----|---|------|---|
| 2 | Me | * | CF₃ | H | 0 | CONH | |
| 3 | * | Me | CF₃ | H | 0 | CONH | 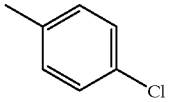 |
| 4 | Me | * | CF₃ | H | 0 | CONH | |
| 5 | * | Me | CF₃ | H | 0 | CSNH | 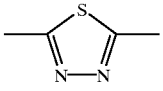 |
| 6 | Me | * | CF₃ | H | 0 | CSNH | |
| 7 | Me | * | CF₂CF₃ | H | 0 | CONH | |
| 8 | * | Me | CF₃ | H | 0 | 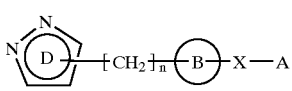 | CONH |
| 9 | Me | * | CF₃ | H | 0 | CONH | |
| 10 | * | Me | CF₃ | H | 0 | 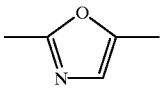 | CONH |

What is claimed is:

1. A pyrazole compound represented by the following general formula (I) or a pharmaceutically acceptable salt thereof $$\underset{N}{\overset{N}{\boxed{D}}}\!-\!\!\mathrm{[CH_2]}_n\!-\!\!\boxed{B}\!-\!\!X\!-\!A \qquad (I)$$

wherein each symbol has the following meaning,

D: 1H-pyrazol-1-yl, which may have 1 to 2 substituents selected from the group consisting of -lower alkyl ("Alk"), -lower alkenyl, -lower alkynyl, halogeno-lower alkyl-, -cycloalkyl, —O-Alk, —COO-Alk and -halogen atom ("Hal"), n: 0, B: 1,4-phenylene, X: —NH—CO—, and A: aryl which may have one or more substituents of group F; mono- or di-cyclic fused heteroaryl selected from the group consisting of thienyl, furanyl, pyrrolyl, imidazolyl, pyrazolyl, thiazolyl, isothiazolyl, oxazolyl, isoxazolyl, tetrazolyl, triazolyl, thiadiazolyl, pyridyl, pyrazinyl, pyrimidinyl, pyridazinyl, indolyl, isoindolyl, isoquinolyl, quinolyl, quinoxanyl, phthalazinyl, imidazo[1,2-a]pyridyl, quinazolinyl and cinnolinyl which may have one or more substituents of group F; cycloalkyl; or Alk, wherein the F group is: -Alk, -lower alkenyl, -lower alkynyl, -Hal, —NH₂, —NH(Alk), —N(Alk)₂, —NO₂, —CN, —OH, —O-Alk, —O—CO-Alk, —SH, —S-Alk, —COO-Alk, —CO-Alk, —CONH₂, —CONH(Alk), —CON(Alk)₂, —SO-Alk, —SO₂-Alk, and —SO₂NH₂, with the proviso that, (1) when D is 3,5-bis(trifluoromethyl)-1H-pyrazol-1-yl, n is 0, B is 1,4-phenylene and X is NHCO, A is a group other than 4-methyl-1,2,3-thiadiazol-5-yl, (2) when D is 1H-pyrazol-1-yl, n is 0, B is 1,4-phenylene and X is NHCO, A is a group other than methyl, (3) when D is 3,5-dimethyl-1H-pyrazol-1-yl, n is 0, B is 1,4-phenylene and X is NHCO, A is a group other than methyl, and (4) when D is 3-methyl-4-bromo-1H-pyrazol-1-yl, n is 0, B is 1,4-phenylene and X is NHCO, A is a group other than methyl.

2. The pyrazole compound or pharmaceutically acceptable salt thereof according to claim 1, wherein D is 1H-pyrazol-1-yl, which may have 1 to 2 substituents selected from -Alk, halogeno-lower alkyl- and —COO-Alk, and A is phenyl which may have one or more substituents selected from the group consisting of -Alk, -Hal, —NH$_2$, —N(Alk)$_2$, —NO$_2$, —CN, —OH, —O-Alk and —COO-Alk; mono- or di-cyclic fused heteroaryl selected from the group consisting of thienyl, pyrrolyl, imidazolyl, thiazolyl, oxazolyl, tetrazolyl, triazolyl, thiadiazolyl, pyridyl, pyrazinyl and isoquinolyl, which may be substituted with one or more Alk; cycloalkyl; or Alk.

3. The pyrazole compound or pharmaceutically acceptable salt thereof according to claim 1, wherein D is 1H-pyrazol-1-yl, substituted with at least one trifluoromethyl group.

4. The pyrazole compound or pharmaceutically acceptable salt thereof according to claim 1, wherein D is 3,5-bis(trifluoromethyl)-1H-pyrazol-1-yl and A is monocyclic heteroaryl selected from the group consisting of thiazolyl, thiadiazolyl, thienyl and pyridyl, which may be substituted with one or more Alk.

5. The pyrazole compound 4'-[3,5-bis(trifluoromethyl)-1H-pyrazol-1-yl]-4-methylthiazole-5-carboxanilide.

6. A pharmaceutical composition which comprises a pharmaceutically effective amount of a pyrazole compound represented by the following general formula (I') or a pharmaceutically acceptable salt thereof and a pharmaceutically acceptable carrier

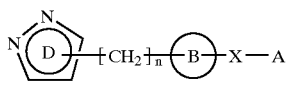

(I')

wherein each symbol has the following meaning,

D: 1H-pyrazol-1-yl, which may have 1 to 2 substituents selected from the group consisting of -Alk, -lower alkenyl, -lower alkynyl, halogeno-lower alkyl-, -cycloalkyl, —O-Alk, —COO-Alk and -Hal, n: 0, B: 1,4-phenylene, X: —NH—CO—, and A: aryl which may have one or more substituents of group F; mono- or di-cyclic fused heteroaryl selected from the group consisting of thienyl, furanyl, pyrrolyl, imidazolyl, pyrazolyl, thiazolyt, isothiazolyl, oxazolyl, isoxazolyl, tetrazolyl, triazolyl, thiadiazolyl, pyridyl, pyrazinyl, pyrimidinyl, pyridazinyl, indolyl, isoindolyl, isoquinolyl, quinolyl, quinoxanyl, phthalazinyl, imidazo[1,2-a]pyridyl, quinazolinyl and cinnolinyl which may have one or more substituents of group F; cycloalkyl; or Alk, wherein the F group is: -Alk, -lower alkenyl, -lower alkynyl, -Hal, —NH$_2$, —NH(Alk), —N(Alk)$_2$, —NO$_2$, —CN, —OH, —O-Alk, —O—CO-Alk, —SH, —S-Alk, —COO-Alk, —CO-Alk, —CONH$_2$, —CONH(Alk), —CON(Alk)$_2$, —SO-Alk, —SO$_2$-Alk, and —SO$_2$NH$_2$, with the proviso that (1) when D is 3,5-bis(trifluoromethyl)-1H-pyrazol-1-yl, n is 0, B is 1,4-phenylene and X is NHCO, A is a group other than 4-methyl-1,2,3-thiadiazol-5-yl, (2) when D is 1H-pyrazol-1-yl, n is 0, B is 1,4-phenylene and X is NHCO, A is a group other than methyl, (3) when D is 3,5-dimethyl-1H-pyrazol-1-yl, n is 0, B is 1,4-phenylene and X is NHCO, A is a group other than methyl, and (4) when D is 3-methyl-4-bromo-1H-pyrazol-1-yl, n is 0, B is 1,4-phenylene and X is NHCO, A is a group other than methyl.

7. The pharmaceutical composition according to claim 6, wherein D is 1H-pyrazol-1-yl substituted with at least one trifluoromethyl group.

8. The pharmaceutical composition according to claim 6, wherein D is 3,5-bis(trifluoromethyl)-1H-pyrazol-1-yl and A is monocyclic heteroaryl selected from the group consisting of thiazolyl, thiadiazolyl, thienyl and pyridyl, which may be substituted with Alk.

9. The pharmaceutical composition which comprises a pyrazole compound according to claim 6, wherein the pyrazole compound is 4'-[3,5-bis(trifluoromethyl)-1H-pyrazol-1-yl]-4-methylthiazole-5-carboxanilide.

10. A method for treating bronchial asthma, which comprises administering a pharmaceutical composition comprising a pyrazole compound represented by the following general formula (I')

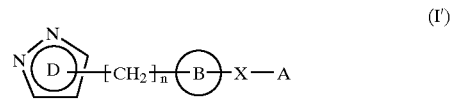

(I')

wherein each symbol has the following meaning,

D: 1H-pyrazol-1-yl, which may have 1 to 2 substituents selected from the group consisting of -Alk, -lower alkenyl, -lower alkynyl, halogeno-lower alkyl-, -cycloalkyl, —O-Alk, —COO-Alk and -Hal, n: 0, B: 1,4-phenylene, X: —NH—CO—, and A: aryl which may have one or more substituents of group F; mono- or di-cyclic fused heteroaryl selected from the group consisting of thienyl, furanyl, pyrrolyl, imidazolyl, pyrazolyl, thiazolyl, isothiazolyl, oxazolyl, isoxazolyl, tetrazolyl, triazolyl, thiadiazolyl, pyridyl, pyrazinyl, pyrimidinyl, pyridazinyl, indolyl, isoindolyl, isoquinolyl, quinolyl, quinoxanyl, phthalazinyl, imidazo[1,2-a]pyridyl, quinazolinyl and cinnolinyl which may have one or more substituents of group F; cycloalkyl; or Alk, wherein the F group is: -Alk, -lower alkenyl, -lower alkynyl, -Hal, —NH$_2$, —NH(Alk), —N(Alk)$_2$, —NO$_2$, —CN, —OH, —O-Alk, —O—CO-Alk, —SH, —S-Alk, —COO-Alk, —CO-Alk, —CONH$_2$, —CONH(Alk), —CON(Alk)$_2$, —SO-Alk, —SO$_2$-Alk, and —SO$_2$NH$_2$, with the proviso that when D is 3,5-bis(trifluoromethyl-1H-pyrazol-1-yl, n is 0, B is 1,4-phenylene and X is NHCO, A is a group other than 4-methyl-1,2,3-thiadiazol-5-yl, or a pharmaceutically acceptable salt thereof, and a pharmaceutically acceptable carrier, in an effective amount for treating said disease in a patient suffering from or susceptible to said disease.

11. The method for treating bronchial asthma according to claim 10, wherein

D is 1H-pyrazol-1-yl, which may have 1 to 2 substituents selected from the group consisting of -Alk, -lower alkenyl, -lower alkynyl, halogeno-lower alkyl-, -cycloalkyl, —O-Alk, —COO-Alk and -Hal, B is 1,4-phenylene, and X is —NH—CO—.

12. The method for treating bronchial asthma which comprises administering a pharmaceutical composition comprising a pyrazole compound according to claim 10, wherein the pyrazole compound is 4'-[3,5-bis(trifluoromethyl)-1H-pyrazol-1-yl]-4-methyithiazole-5-carboxanilide.

13. A method for treating rheumatoid arthritis, which comprises administering a pharmaceutical composition comprising a pyrazole compound represented by the following general formula (I')

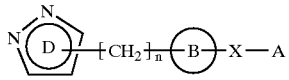
(I')

wherein each symbol has the following meaning,

D: 1H-pyrazol-1-yl, which may have 1 to 2 substituents selected from the group consisting of -Alk, -lower alkenyl, -lower alkynyl, halogeno-lower alkyl-, -cycloalcyl, —O-Alk, —COO-Alk and -Hal, n: 0, B: 1,4-phenylene, X: —NH—CO—, and A: aryl which may have one or more substituents of group F; mono- or di-cyclic fused heteroaryl selected from the group consisting of thienyl, furanyl, pyrrolyl, imidazolyl, pyrazolyl, thiazolyl, isothiazolyl, oxazolyl, isoxazolyl, tetrazolyl, triazolyl, thiadiazolyl, pyridyl, pyrazinyl, pyrimidinyl, pyridazinyl, indolyl, isoindolyl, isoquinolyl, quinolyl, quinoxanyl, phihalazinyl, imidazo[1,2-a]pyridyl, quinazolinyl and cinnolinyl which may have one or more substituents of group F; cycloalkyl; or -Alk, wherein the F group is: -Alk, -lower alkenyl, -lower alkynyl, -Hal, —NH$_2$, —NH(Alk), —N(Alk)$_2$, —NO$_2$, —CN, —OH, —O-Alk, —O—CO-Alk, —SH, —S-Alk, —COO-Alk, —CO-Alk, —CONH$_2$, —CONH(Alk), —CON(Alk)$_2$, —SO-Alk, —SO$_2$-Alk, and —SO$_2$NH$_2$, with the proviso that when D is 3,5-bis(trifluoromethyl)-1H-pyrazol-1-yl, n is 0, B is 1,4-phenylene and X is NHCO, A is a group other than 4-methyl-1,2,3-thiadiazol-5-yl, or a pharmaceutically acceptable salt thereof, and a pharmaceutically acceptable carrier, in an effective amount for treating said disease in a patient suffering from or susceptible to said disease.

14. The method for treating rheumatoid arthritis according to claim 13, wherein

D is 1H-pyrazol-1-yl, which may have 1 to 2 substituents selected from the group consisting of -Alk, -lower alkenyl, -lower alkynyl, halogeno-lower alkyl-, -cycloalkyl, —O-Alk, —COO-Alk and -Hal, B is 1,4-phenylene, and X is —NH—CO—.

15. The method for treating rheumatoid arthritis which comprises administering a pharmaceutical composition comprising a pyrazole compound according to claim 13, wherein the pyrazole compound is 4'-[3,5-bis(trifluoromethyl)-1H-pyrazol-1-yl]-4-methylthiazole-5-carboxanilide.

* * * * *